(12) United States Patent
Koblish

(10) Patent No.: US 12,089,891 B2
(45) Date of Patent: *Sep. 17, 2024

(54) MULTI-USE ENDOCARDIAL ABLATION CATHETER

(71) Applicant: Pfix, Inc., Menlo Park, CA (US)

(72) Inventor: Josef Koblish, Sunnyvale, CA (US)

(73) Assignee: Pfix, Inc., Menlo Park, CA (US)

( * ) Notice: Subject to any disclaimer, the term of this patent is extended or adjusted under 35 U.S.C. 154(b) by 494 days.

This patent is subject to a terminal disclaimer.

(21) Appl. No.: 17/473,408

(22) Filed: Sep. 13, 2021

(65) Prior Publication Data
US 2022/0192740 A1 Jun. 23, 2022

Related U.S. Application Data

(63) Continuation of application No. 17/127,676, filed on Dec. 18, 2020, now Pat. No. 11,147,617.

(51) Int. Cl.
*A61B 18/14* (2006.01)
*A61B 18/00* (2006.01)
*A61B 18/24* (2006.01)

(52) U.S. Cl.
CPC ...... *A61B 18/1492* (2013.01); *A61B 2018/00351* (2013.01); *A61B 2018/00357* (2013.01); *A61B 2018/00375* (2013.01); *A61B 2018/00577* (2013.01); *A61B 2018/00601* (2013.01); *A61B 2018/00642* (2013.01); *A61B 2018/00702* (2013.01); *A61B 2018/00708* (2013.01); *A61B 2018/00779* (2013.01);
(Continued)

(58) Field of Classification Search
CPC ..... A61B 18/1492; A61B 18/14; A61B 18/24; A61B 2018/00351; A61B 2018/00357; A61B 2018/00375; A61B 2018/00577; A61B 2018/00601; A61B 2018/00642; A61B 2018/00702; A61B 2018/00708; A61B 2018/00779; A61B 2018/00922; A61B 2018/1405; A61B 2018/1407; A61B 2018/00839; A61B 2018/1475
See application file for complete search history.

(56) References Cited

U.S. PATENT DOCUMENTS 6,142,994 A * 11/2000 Swanson ............ A61B 18/1492
606/49
2009/0093809 A1* 4/2009 Anderson .......... A61B 18/1482
606/41
(Continued)

*Primary Examiner* — Adam Z Minchella
*Assistant Examiner* — Ana Veruska Guerrero
(74) *Attorney, Agent, or Firm* — Vista IP Law Group, LLP

(57) ABSTRACT

A method comprises introducing an ablation catheter assembly into a heart chamber of the patient, deploying an ablative loop structure from an elongated shaft of the ablation catheter assembly, placing the ablative loop structure in an expanded geometry, disposing the expanded ablative loop structure on the endocardial tissue around an ostium of a blood vessel extending from the heart chamber, activating the ablative loop structure, thereby creating a circumferential lesion around the ostium of the blood vessel, disposing the ablative shaft distal end, when the ablative loop structure is housed within the elongated shaft, at a target region of the endocardial tissue remote from the ostium of the blood vessel, and activating the ablative shaft distal end, thereby creating another lesion at the target region.

9 Claims, 17 Drawing Sheets

(52) U.S. Cl.
CPC ..... *A61B 2018/00922* (2013.01); *A61B 18/14* (2013.01); *A61B 2018/1405* (2013.01); *A61B 2018/1407* (2013.01); *A61B 18/24* (2013.01)

(56) References Cited

U.S. PATENT DOCUMENTS

| | | | |
|---|---|---|---|
| 2015/0342675 A1* | 12/2015 | Highsmith | A61B 18/1492 606/41 |
| 2017/0127676 A1* | 5/2017 | Menges | A01N 43/80 |
| 2019/0231421 A1* | 8/2019 | Viswanathan | A61N 1/056 |

* cited by examiner

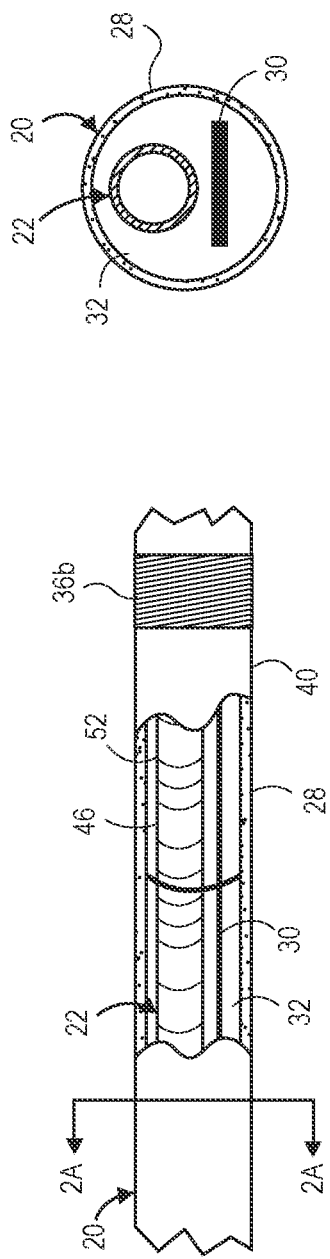
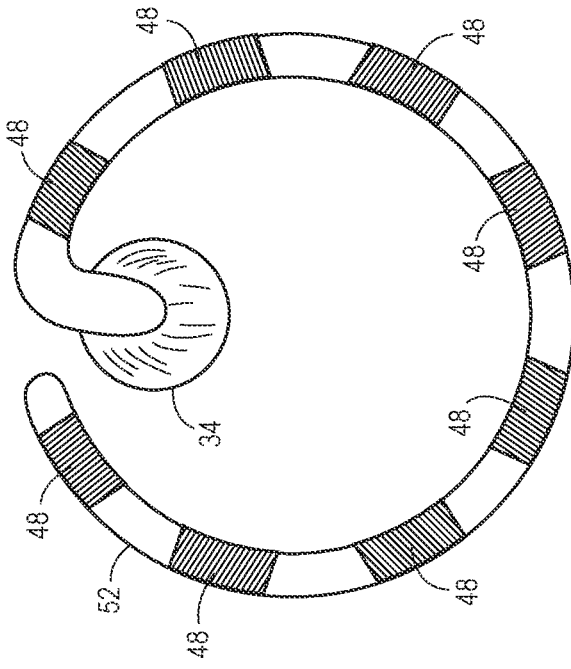
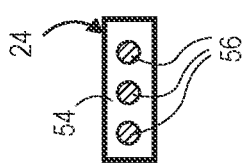
FIG. 2A
FIG. 4
FIG. 2
FIG. 3

MULTI-USE ENDOCARDIAL ABLATION CATHETER

RELATED APPLICATION DATA

The present application is a continuation of U.S. patent application Ser. No. 17/127,676, filed on Dec. 18, 2020, which is expressly incorporated herein by reference.

FIELD OF THE INVENTION

The present invention relates generally to medical devices for use in cardiological procedures, and more specifically, to catheters to be used for cardiac ablation and electrophysiological procedures.

BACKGROUND OF THE INVENTION

Cardiac arrhythmias are a widespread medical condition facing physicians today. Their most frequent cause is an abnormal routing of electricity through the cardiac tissue. In patients with normal sinus rhythm, the har, which is comprised of atrial, ventricular, and excitatory conduction tissue, is electrically excited to beat in a synchronous, patterned fashion. In patients with cardiac arrhythmias, abnormal regions of cardiac tissue aberrantly conductive to adjacent tissue, thereby disrupting the cardiac cycle into an asynchronous cardiac rhythm. Such abnormal conduction had been previously known to occur at various regions of the heart, for example, in the region of the sino-atrial (SA) node, along the conduction pathways of the atrioventricular (AV) node and the Bundle of His, or in the cardiac muscle tissue forming the walls of the ventricular and atrial cardiac chambers. Cardiac arrhythmias, including atrial arrhythmia, may be of a multiwavelet reentry type, characterized by multiple asynchronous loops of electrical impulses that are scattered about the atrial chamber and are often self-propagating. In the alternative or in addition to the multiwavelet reentrant type, cardiac arrhythmias may also have a focal region, such as when an isolated region of tissue in an atrium fires autonomously in a rapid, repetitive fashion.

Atrial fibrillation (AF) is by far the most common arrhythmic heart disorder in the United States. AF may affect approximately 2 million people and can account for approximately 500,000 hospital admissions a year. A host of clinical conditions may result from the irregular cardiac function and resulting hemodynamic abnormalities associated with AF, including stroke, heart failure, and other thromboembolic events. In fact, AF is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle, which thereafter pumps the embolism into the cerebral circulation where a stroke results. Accordingly, numerous procedures for treating atrial arrhythmias have been developed, including pharmacological, surgical, and catheter ablation procedures.

While most patients with AF can be managed adequately with pharmacological therapy, a large number of patients can develop complications to the medicines used to treat disease including fatigue, lightheadedness, or substantial bleeding. In some cases, drugs that are used to prevent AF may not be very effective and can have potentially serious long-term complications. While several surgical approaches, such as the Cox-Maze procedure, have been developed for the purpose of treating or preventing different types of cardiac arrhythmias, they are highly invasive. Ablation is now widely used as the preferred treatment. Typically, a physician places an endocardial catheter inside the heart at a location where cells are giving off abnormal electrical signals. The endocardial catheter is activated according to various known modes of operation, such that the adjacent targeted tissue is ablated to create contiguous electrical-isolation lines that renders the tissue non-conductive, halting the spread of improper cardiac signals.

Various types of different catheters may be utilized to create different electrical-isolation lines. For example, a catheter having a loop structure carrying electrodes can be employed to create circumferential electro-isolation lines along the atrial wall around the ostia of pulmonary veins. As another example, a catheter carrying a tip electrode can be employed to incrementally create electro-isolation lines along the atrial wall. As still another example, a catheter carrying a series of electrodes along its distal end can be employed to simultaneously create electro-isolation lines along the atrial wall.

While catheter ablation may be highly successful in the treatment of conditions where the offending conductive disturbance is well known and localized, such as accessory conductive pathways or atrial flutter, its success in treatment the most common arrhythmia of AF has been modest. The procedure can require several hours of anesthesia, radiation, and the use of multiple catheters with their attendant risks even in the hands of skilled operators. There are therefore needs for an ablation catheter that simplifies the mechanics of the creation of the contiguous electrical-isolation lines in the ablation procedure. Such an improved ablation catheter may increase the success rate of the procedure for patients while greatly reducing the associated cost of these procedures.

SUMMARY

In accordance with a first aspect of the present inventions, an ablation catheter assembly comprises an outer ablation catheter and an inner ablation catheter slidably disposed within the inner lumen of the outer ablation catheter. The outer ablation catheter comprises an elongated shaft having a proximal shaft section and a distal shaft section, an inner lumen extending through the proximal shaft section and the distal shaft section, a distal tip port in communication with the inner lumen, and at least one ablative element disposed on the distal shaft section.

The inner ablation catheter comprises an elongated inner member having a proximal member section and a distal member section, and a plurality of ablative elements disposed along the distal member section. The distal member section is configured for being deployed from the distal tip port when the inner ablation catheter is distally slid within the inner lumen of the outer ablation catheter, thereby placing the distal member section into an expanded loop geometry.

The ablative elements of the outer ablation catheter may, e.g., comprise a tip ablative element and/or a linear array of electrodes disposed along the distal shaft section. Each of the ablative elements of the outer ablation catheter and the inner ablation catheter may, e.g., be an electrode.

In one embodiment, the distal member section is configured for being retracted within the distal tip port when the inner ablation catheter is proximally slid within the inner lumen of the outer ablation catheter, thereby placing the distal member section into a low-profile geometry. In another embodiment, the distal member section is pre-shaped to be placed in the expanded loop geometry (e.g., a circular geometry). The distal member section, when in the expanded loop geometry, may have a diameter in the range of, e.g., 10-20 millimeters. In still another embodiment, the distal member section, when in the expanded loop geometry, may reside in a plane orthogonal to a longitudinal axis of the elongated shaft. In yet another embodiment, the shaft distal end is steerable. In this case, the ablation catheter assembly may further comprise a pull wire affixed to the shaft distal end. The pull wire may be disposed exterior to the elongated shaft. The ablation catheter assembly may further comprise a stiffening plate disposed within the shaft distal end. The distal member section may be less laterally stiff than the stiffening plate. In yet another embodiment, the ablation catheter assembly further comprises a handle assembly having a handle body and an actuator carried by the handle body. The proximal shaft section is affixed to the handle body, and the proximal member section is operatively associated with the actuator to deploy the distal member section from the distal tip port.

In accordance with a second aspect of the present inventions, a tissue ablation system comprises the ablation catheter assembly and a source of ablation operatively coupled to the ablation catheter assembly. In one embodiment, the tissue ablation system further comprises a mapping processor operatively coupled to the ablation catheter assembly.

In accordance with a third aspect of the present inventions, a method of using the ablation catheter assembly comprises introducing the ablation catheter assembly into a heart chamber (e.g., a left atrium) of a patient (e.g., a patient having cardiac arrhythmia), while the distal member section is in the low-profile geometry within the inner shaft lumen. The method further comprises distally sliding the elongated inner member within the inner shaft lumen, thereby deploying the distal member section from the distal tip port, and placing the distal member section into the expanded loop geometry. In one method, the distal member section automatically assumes the expanded loop geometry in response to deploying the distal member section from the distal tip port.

The method further comprises disposing the distal member section, when in the expanded loop geometry, on the endocardial tissue around an ostium of a blood vessel (e.g., a pulmonary vein) extending from the heart chamber, and activating the plurality of ablative elements, thereby creating a circumferential lesion around the ostium of the blood vessel. The method further comprises disposing the electrode(s), when the distal member section is in the low-profile geometry within the elongated shaft, at a target region of the endocardial tissue remote from the ostium of the blood vessel, and activating the ablative element(s), thereby creating another lesion at the target region. The circumferential lesion and the other lesion may, e.g., treat the cardiac arrhythmia of the patient.

One method further comprises proximally sliding the elongated inner member within the inner shaft lumen, thereby retracting the distal member section into the distal tip port. For example, the method may comprise retracting the distal member section into the distal tip port after creating the circumferential lesion around the ostium of the blood vessel, but prior to disposing the distal shaft section on the target site of the endocardial tissue.

In one method, the target region of the endocardial tissue at which the lesion is created is a target line, in which case, the other lesion may be a linear lesion. In this case, the ablation element(s) may comprise a tip ablation element, and disposing the ablative element(s) at the target region of the endocardial tissue and activating the ablative element(s) may comprise iteratively disposing the tip ablation element at different points along the target line of the endocardial tissue and activating the tip ablation element, thereby iteratively creating the other lesion along the target line. The ablation element(s) may comprise a linear array of electrodes disposed along the distal shaft section, and disposing the ablative element(s) at the target region of the endocardial tissue and activating the ablative element(s) may comprise disposing the linear array of electrodes along the target line of the endocardial tissue and activating the linear array of electrodes, thereby creating the other lesion along the target line.

In accordance with a fourth aspect of the present inventions, a method of ablating endocardial tissue of a patient (e.g., a patient having cardiac arrhythmia) using an ablation catheter assembly having an elongated shaft having an ablative shaft distal end, and an ablative loop structure housed within the elongated shaft is provided. This method comprises introducing the ablation catheter assembly into a heart chamber (e.g., a left atrium) of the patient, deploying the ablative loop structure from the elongated shaft, and placing the ablative loop structure in an expanded geometry. In one method, the ablative loop structure assumes the expanded geometry in response to deploying the ablative loop structure from the elongated shaft.

The method further comprises disposing the expanded ablative loop structure on the endocardial tissue around an ostium of a blood vessel (e.g., a pulmonary vein) extending from the heart chamber, and activating the ablative loop structure, thereby creating a circumferential lesion around the ostium of the blood vessel. The method further comprises disposing the ablative shaft distal end, when the ablative loop structure is housed within the elongated shaft, at a target region of the endocardial tissue remote from the ostium of the blood vessel, and activating the ablative shaft distal end, thereby creating another lesion at the target region. The circumferential lesion and the other lesion may, e.g., treat the cardiac arrhythmia of the patient.

One method further comprises retracting the ablative loop structure within the elongated shaft after creating the circumferential lesion around the ostium of the blood vessel, but prior to disposing the ablative shaft distal end on the target site of the endocardial tissue. In another method, the target region of the endocardial tissue at which the lesion is created is a target line, in which case, the other lesion may be a linear lesion. In this case, the ablative shaft distal end may have an ablative distal tip, and disposing the ablative shaft distal end at the target region of the endocardial tissue and activating the ablative shaft distal end may comprise iteratively disposing the ablative distal tip at different points along the target line of the endocardial tissue and activating the ablative distal tip, thereby iteratively creating the other lesion along the target line. Disposing the ablative shaft distal end at the target region of the endocardial tissue and activating the ablative loop structure may comprise disposing the ablative shaft distal end along the target line of the endocardial tissue and activating the ablative shaft distal end, thereby creating the other lesion along the target line.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of preferred embodiments of the present invention, in which similar elements are referred to by common reference numerals. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 2 is a partially cutaway view of the EP catheter assembly of the tissue ablation system of FIGS. 1A-1C;

FIG. 2A is a cross-sectional view of the EP catheter assembly of FIG. 2, taken along the line 2A-2A;

FIG. 3 is a cross-sectional view of a push/pull steering wire used by the EP ablation system of the tissue ablation system of FIGS. 1A-1C;

FIG. 4 is a front view of a distal section of the inner ablation catheter deployed from the outer ablation catheter of the tissue ablation system of FIGS. 1A-1C;

DETAILED DESCRIPTION OF THE ILLUSTRATED EMBODIMENTS

Figure 1A:
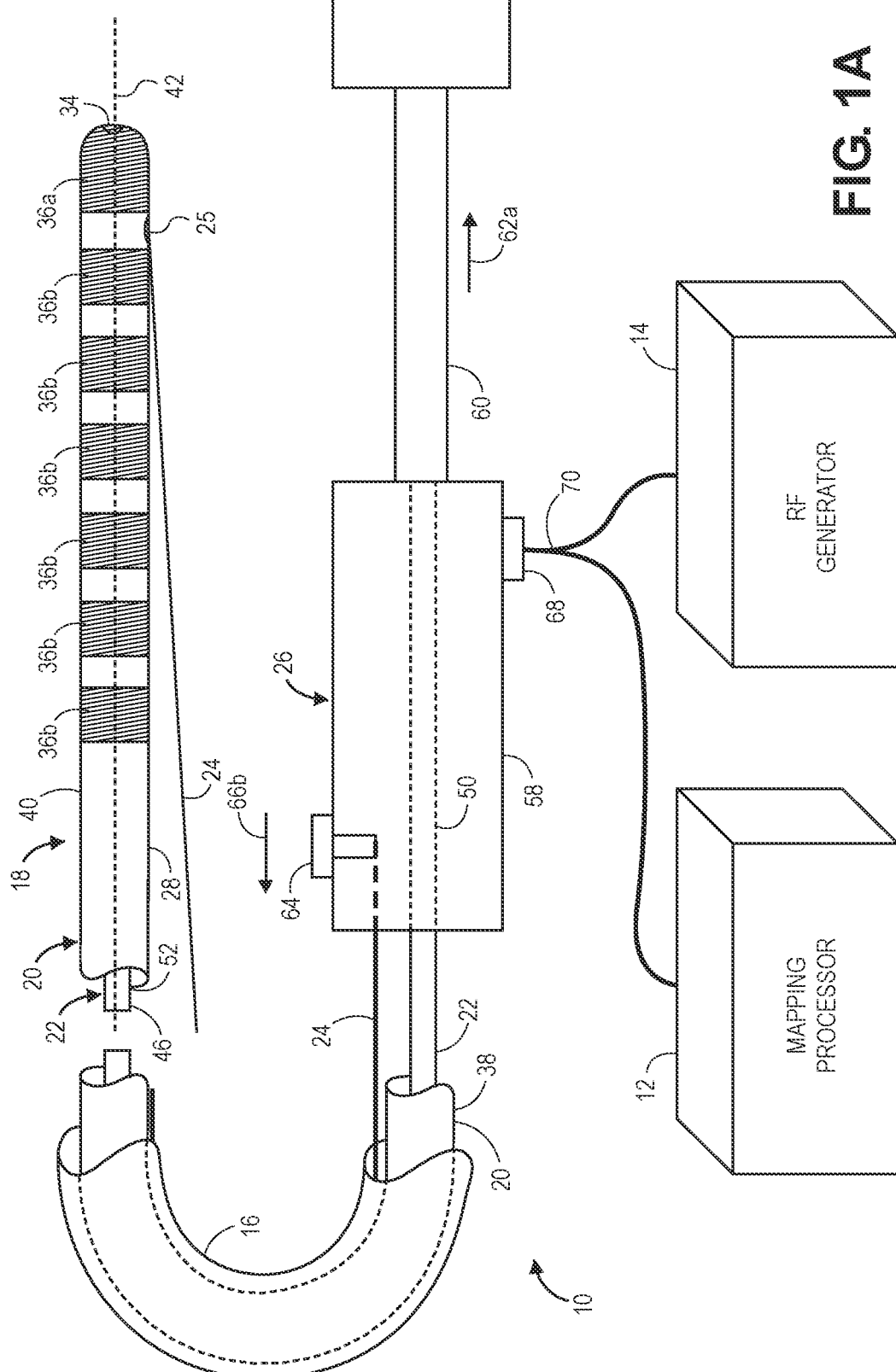
FIG. 1A is a plan view of a tissue ablation system constructed in accordance with one embodiment of the present inventions, particularly showing an electrophysiology (EP) catheter assembly with an inner ablation catheter retracted within an outer ablation catheter.

Referring to FIGS. 1A-1C, 2, 2A, and 3-4, one exemplary embodiment of a tissue ablation system 10 capable of creating lesions on the endocardial tissue of a patient to treat cardiac arrythmia suffered by the patient will be described. Significantly, the ablation system 10 is capable of creating different types of lesions on the endocardial tissue of the patient without requiring the use of multiple catheters, thereby decreasing the surgical procedure time. Although the tissue ablation system 10 lends itself well to the creation of endocardial lesions within the left atrium of the patient to treat atrial fibrillation (AF), the tissue ablation system 10 may be used to create endocardial lesions in any heart chamber of the heart to treat any type of cardiac arrythmias (including atrial flutter or ventricular tachycardia) from which the patient may suffer. Furthermore, the tissue ablation system 10 is not limited to use in heart chambers, but may be used within any body lumen, chamber, or cavity for diagnostic and therapeutic purpose in instances where access to interior bodily regions is obtained through, for example, the vascular system or alimentary canal. Furthermore, the tissue ablation system 10 is not limited to the treatment of ailments in the heart, but can be used to treat ailments of the gastrointestinal tract, prostate, brain, gall bladder, uterus, and other regions of the body.

The ablation system 10 generally comprises a mapping processor 12, an ablation source 14, a guide sheath 16, and an electrophysiology (EP) catheter assembly 18 operably coupled to the mapping processor 12 and ablation source 14.

The mapping processor 12 is configured for detecting, processing, and recording electrical signals within the heart via the EP catheter assembly 18. Based on these electrical signals, a physician can identify the specific target tissue sites within the heart, and ensure that the arrhythmia causing substrates have been electrically isolated by the ablative treatment. Based on the detected electrical signals, the mapping processor 12 outputs electrocardiograms (ECGs) to a display (not shown), which can be analyzed by the user to determine the existence and/or location of arrhythmia substrates within the heart and/or determine the location of the EP catheter assembly 18 within the heart. In an optional embodiment, the mapping processor 12 can generate and output an isochronal map of the detected electrical activity to the display for analysis by the user. Such mapping techniques are well known in the art, and thus for purposes of brevity, will not be described in further detail.

The ablation source 14 is configured for delivering ablation energy to the EP catheter assembly 18 in a controlled manner in order to ablate the target tissue sites identified by the mapping processor 12. In the illustrated embodiment, the ablation source 14 takes the form of a radio frequency (RF) generator. The RF generator 14 may be a conventional RF power supply that operates at a suitable frequency (e.g., in the range of 200 KHz to 1.25 MHz) with a conventional sinusoidal or non-sinusoidal wave form. Such power supplies are available from many commercial suppliers, such as Valleylab, Aspen, and Bovie. The RF generator 12 will typically be operated at the lower end of the voltage and power capability (e.g., below 150 volts, usually between 50 volts and 100 volts, and at a power from 20 watts to 200 watts). Ablation of tissue within the heart is well known in the art, and thus for purposes of brevity, the RF generator 14 will not be described in further detail. In one embodiment, the RF generator may be operated a Pulsed Field Ablation (PFA) mode to cause irreversible electroporation of the tissue. Alternatively, other types of ablation sources besides the RF generator 14 can be used, e.g., a microwave generator, an ultrasound generator, a cryoablation generator, and a laser or other optical generator.

The EP catheter assembly 18 may be advanced though the guide sheath 16 to the target location. The guide sheath 16, which should be lubricious to reduce friction during movement of the EP catheter assembly 18, may be advanced over a guidewire in conventional fashion. Alternatively, a steerable sheath may be provided. With respect to materials, the proximal portion of the guide sheath 16 is preferably a Pebax® material and stainless steel braid composite, and the distal portion is a more flexible material, such as unbraided Pebax®, for steering purposes. The guide sheath 16 should also be stiffer than the EP catheter assembly 18. A sheath introducer (not shown) may be used when introducing the EP catheter assembly 18 into the guide sheath 16. The guide sheath 16 preferably includes a radio-opaque compound, such as barium, so that the guide sheath 16 can be observed using fluoroscopic or ultrasound imaging, or the like. Alternatively, a radio-opaque marker (not shown) can be placed at the distal end of the guide sheath 16. Guide sheaths are well known in the art, and thus for purposes of brevity, the guide sheath 16 will not be described in further detail.

The EP catheter assembly 18 is configured for being introduced through the vasculature of the patient, and into the left atrium of the heart, were it can be used to map and ablate target regions in the endocardial tissue. Although the EP catheter assembly 18 is catheter-based, alternative embodiments may be adapted for use in conjunction with hand-held surgical devices (or "surgical probes"), in which case, the distal end of a surgical probe may be placed directly in contact with the targeted tissue area by a physician during a surgical procedure, such as open-heart surgery. Here, access may be obtained by a way of a thoracotomy, median sternotomy, or thoracostomy.

The EP catheter assembly 18 generally comprises an outer ablation catheter 20, an inner ablation catheter 22, a steering element 24, and a handle assembly 26.

The outer ablation catheter 20 comprises an elongated shaft 28, a steering plate 30 (shown best in FIGS. 2 and 2A), an inner lumen 32 (shown best in FIGS. 2 and 2A), a distal tip port 34, and at least one ablative element 36.

The elongated shaft 28 is preferably about 5 French to 9 French in diameter, and between 80 cm to 150 cm in length. The elongated shaft 28 preferably has a cross-sectional geometry that is circular. However, other cross-sectional shapes, such as elliptical, rectangular, triangular, and various customized shapes, may be used as well. The elongated shaft 28 is preferably flexible so that it is capable of winding through a tortuous path that leads to a target site, i.e., an area within the heart. Alternatively, the elongated shaft 28 may be semi-rigid, i.e., by being made of a stiff material, or by being reinforced with a coating or coil, to limit the amount of flexing. The elongated shaft 28 is preferably preformed of an inert, resilient plastic material that retains its shape and does not soften significantly at body temperature; for example, Pebax®, polyethylene, or Hytrel® (polyester). Alternatively, the elongated shaft 28 may be made of a variety of materials, including, but not limited to, metals and polymers.

The elongated shaft 28 has a proximal section 38 and a distal section 40. The proximal section 38 of the elongated shaft 28 is preferably formed of a material that provides it with good torque transmission qualities. For example, the proximal section 38 may be composed of a biocompatible thermoplastic (e.g., Pebax®, (polyether block amide), polyethylene, or Hytrel® (polyester)) and stainless-steel composite, which may include an elongate guide coil. In contrast, for steering purposes, the distal section 40 of the elongated shaft 28 is composed of a more flexible material, such as an unbraided biocompatible thermoplastic (e.g., Pebax®, (polyether block amide), polyethylene, or Hytrel® (polyester)). The proximal section 38 and distal section 40 of the elongated shaft 28 may be bonded together at an interface with an overlapping thermal bond or adhesively butt bonded together end to end over a sleeve. In an optional embodiment, the proximal section 38 and distal section 40 of the elongated shaft 28 are radiopaque to enable visualization of the EP catheter assembly 18 under fluoroscopy. For example, the metallic nature of the proximal section 38 may inherently provide radiopaqueness to the EP catheter assembly 18, while the distal section 40 may be loaded within radiopaque particles, such as tungsten or bismuth. In an optional embodiment, the elongated shaft 28 has an intermediate section (not shown) that transitions the higher stiffness of the proximal section 38 to the lower stiffness of the distal section 40.

Figure 1B:
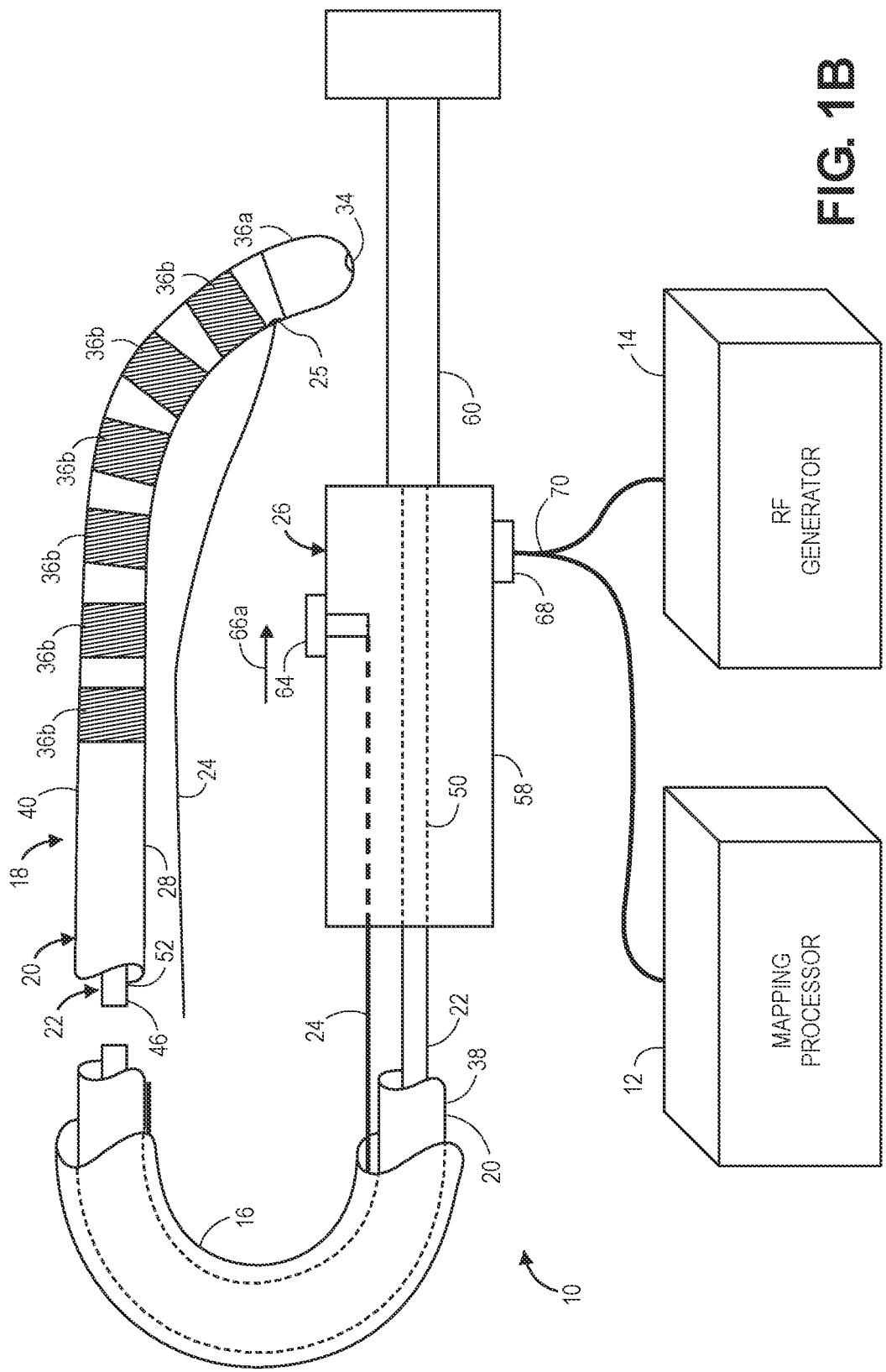
FIG. 1B is a plan view of the tissue ablation system of FIG. 1A, particularly showing deflection of the outer ablation catheter.

In the illustrated embodiment, the distal section 40 of the elongated shaft 28 is steerable. To this end, the steering plate 30 facilitates bending of the distal section 40 of the elongated shaft 28 in a consistent and repeatable plane, as illustrated in FIG. 1B. In this embodiment, the steering plate 30 has a rectangular cross-section affixed within the elongated shaft 28 along the distal section 40. The thickness of the rectangular steering plate 30 is preferably between about 0.010 inch and about 0.015 inch. The steering plate 30 may be composed, e.g., Nickel Titanium (commercially available under the trade name Nitinol), a high yield strength steel (17-7 PH®), or a resilient injection molded plastic. In one embodiment, the steering plate 30 may reside within a separate polymeric tube (not shown). In an alternative embodiment, the steering plate 30 may be embedded in the wall of the elongated shaft 28. The lateral stiffness of the combination of the elongated shaft 28 and the steering plate 30 extending along the distal section 40 is less than the lateral stiffness of the elongated shaft 28 extending along the proximal section 38. Optionally, in the case where the elongated shaft 28 has an intermediate section between the proximal section 38 and the distal section 40, the steering plate 30 may have a geometric profile along a longitudinal axis 42 of the elongated shaft 28 that tapers down in the distal direction along the intermediate section, such that the steering plate 30 transitions the higher lateral stiffness of the proximal section 38 to the lower lateral stiffness of the distal section 40 in a gradual manner.

The inner lumen 32 of the outer ablation catheter 20 extends through the proximal section 38 and distal section 40 of the elongated shaft 28. The inner lumen 32 is sized such that it can house the inner ablation catheter 22 during use. The distal tip port 34 is in communication with the inner lumen 32. In the illustrated embodiment, the ablative element(s) 36 comprises a linear array of ablative elements disposed along the distal section 40 of the elongated shaft 28. As a result, a distal ablative structure is formed at the distal end of the outer ablation catheter 20.

In the illustrated embodiment, the linear array of ablative elements 36 comprises a cap electrode 36a and a plurality of ring electrodes 36b, although in alternative embodiments, the ablative elements 36 can take other forms, e.g., chemical ablation lumens, ultrasonic transducers, microwave electrodes, ohmically heated hot wires, optical emitters, etc. The electrodes 36 may have any suitable length, e.g., in the range between 4 mm and 10 mm. The electrodes 36 may be composed of any suitable biocompatible, electrically conductive, material, e.g., platinum, gold, or stainless steel. In the illustrated embodiment, the ring electrodes 36b numbers six, although in other embodiments, any plural number of ring electrodes 36b can be provided.

In the illustrated embodiment, the electrodes 36 are solid discrete elements, although in alternative embodiments, the electrodes 36 may be formed by coating the exterior surface of the distal section 40 of the elongated shaft 28 with an electrically conducting material, like platinum or gold. The coating can be applied using sputtering, ion beam deposition, or equivalent techniques. The electrodes 36 can also be formed with a conductive ink compound that is pad printed onto distal section 40 of the elongated shaft 28. A preferred conductive ink compound is a silver-based flexible adhesive conductive ink (polyurethane binder), however other metal-based adhesive conductive inks such as platinum-based, gold-based, copper-based, etc., may also be used to form electrodes 34. Such inks are more flexible than epoxy-based inks. In another alternative embodiment, the ring electrodes 36*b* may take the form of wound, spiral coils. The coils can be made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility.

The electrodes 36 are electrically coupled to the mapping processor 12 (shown in FIG. 1), so that electrical events in myocardial tissue can be sensed for the creation of electrograms or monophasic action potentials (MAPs), or alternatively, isochronal electrical activity maps. To this end, signal wires (not shown) are respectively connected to the electrodes 36 using suitable means, such as soldering or welding. The signal wires are passed in a conventional fashion through a lumen (not shown) extending through the elongated shaft 28, where they are electrically coupled to the mapping processor 12 via the handle assembly 26, as will be described in further detail below. The electrodes 36 are also electrically coupled to the RF generator 14, so that the RF generator 14 may conduct coagulating energy to the electrodes 36. To this end, ablation wires (not shown) are respectively connected to the electrodes 36 using suitable means, such as soldering or welding. The ablation wires are passed in a conventional fashion through a lumen (not shown) extending through the elongated shaft 28, where they are electrically coupled to the RF generator 14 via the handle assembly 26, as will be described in further detail below.

The inner ablation catheter 22 is slidably disposed within the inner lumen 32 of the outer ablation catheter 20. The inner ablation catheter 22 comprises an elongated member 46 and a plurality of ablation elements 48 (shown in FIGS. 1B and 4).

The elongated member 46 is preferably about 3 French to 4 French in diameter, so that the outer ablation catheter 20 that houses the inner ablation catheter 22 assumes a small profile. The elongated member 46 preferably has a cross-sectional geometry that is circular. However, other cross-sectional shapes, such as elliptical, rectangular, triangular, and various customized shapes, may be used as well. The elongated member 46 is formed of a flexible spline composed of a resilient, biologically inert material, such as Nitinol). Thus, the elongated member 46 is configured for bending and conforming to the endocardial tissue that it contacts.

Figure 1C:
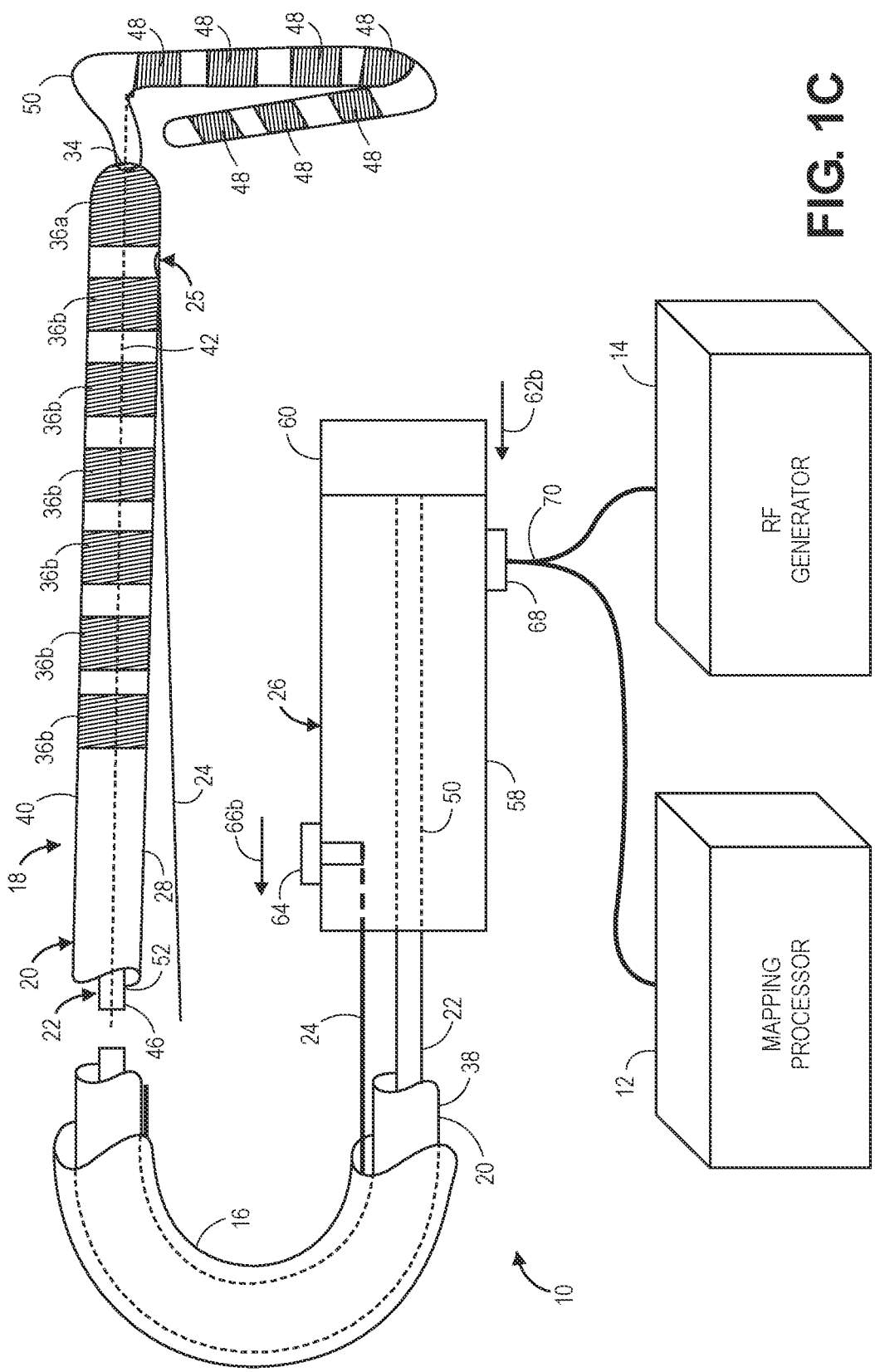
FIG. 1C is a plan view of the tissue ablation system of FIG. 1A, particularly showing the inner ablation catheter deployed from the outer ablation catheter.
Figure 5:
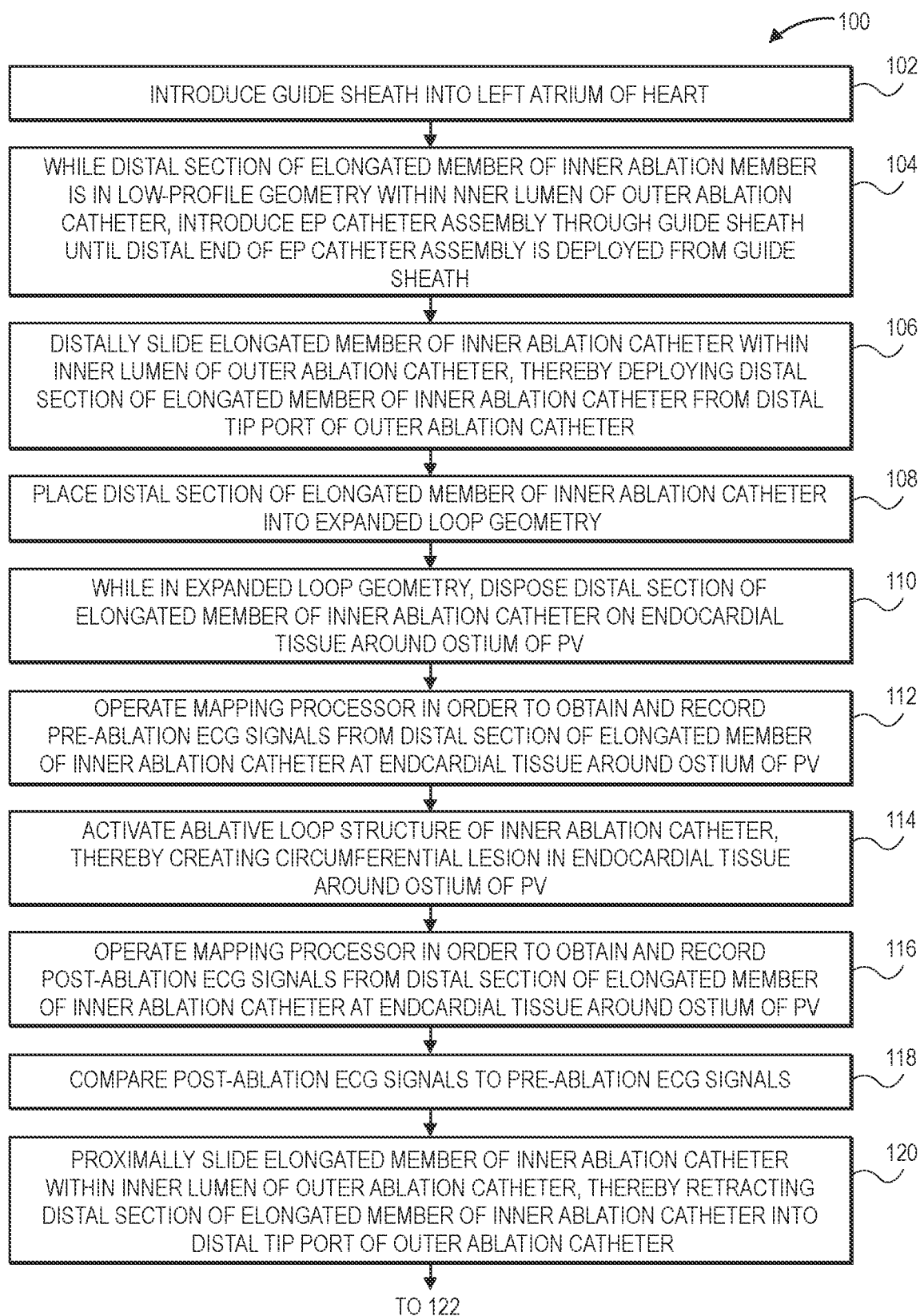
FIG. 5 is a flow diagram of one method of operating the tissue ablation system of FIGS. 1A-1C to create lesions within the left atrium of a heart.
Figure 5:
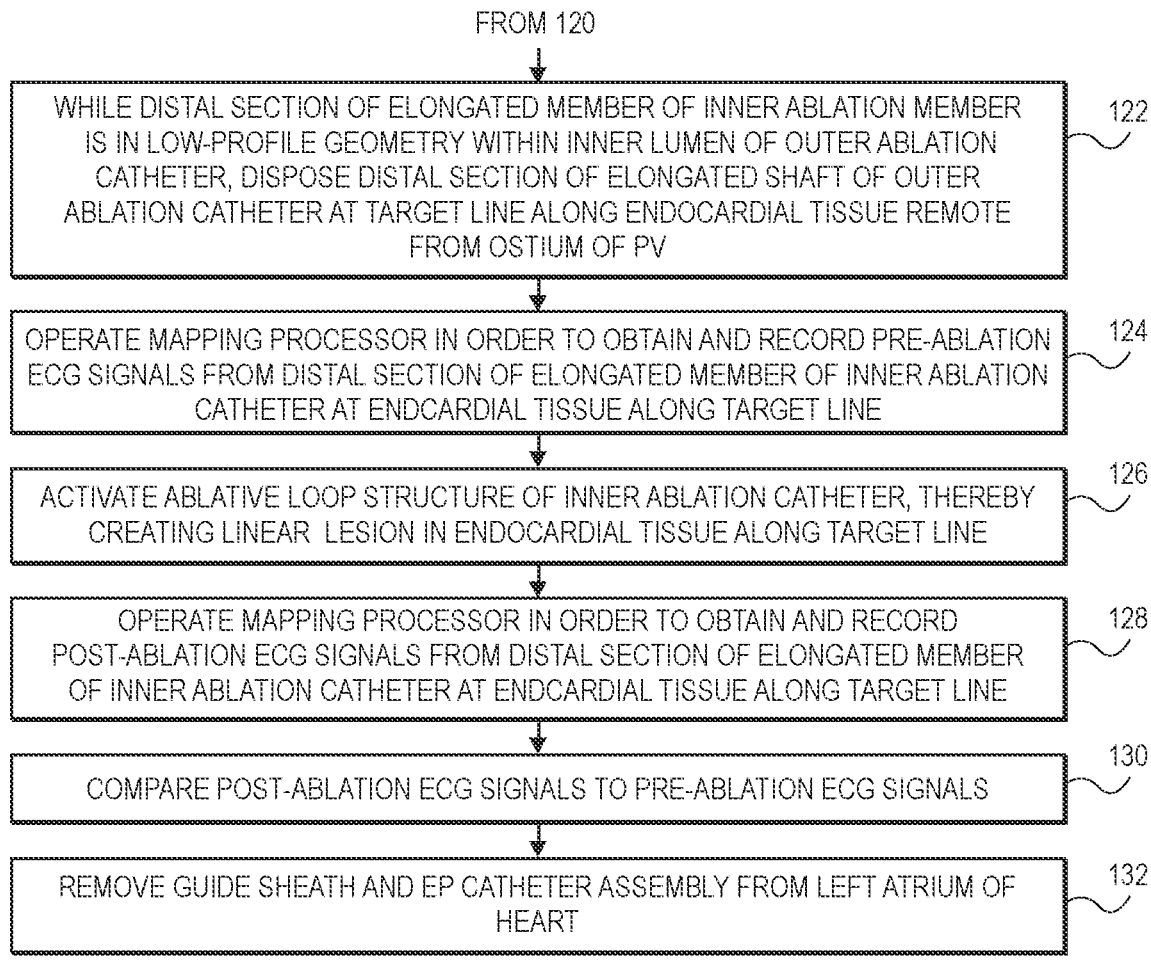

The elongated member 46 has a proximal section 50 and a distal section 52 (see FIG. 1C). The distal section 52 is configured for being retracted within the distal tip port 34 of the outer ablation catheter 20 into a low-profile geometry (shown in FIG. 2) in response to proximally sliding the inner ablation catheter 22 within the inner lumen 32 of the outer ablation catheter 20 and for being deployed form the distal tip port 34 of the outer ablation catheter 20 into an expanded loop geometry (shown in FIG. 4) in response to distally sliding the inner ablation catheter 22 within the inner lumen 32 of the outer ablation catheter 20. In the illustrated embodiment, the expanded loop geometry of the distal section 52 of the elongated member 46 is circular, and resides in a plane that is orthogonal to a longitudinal axis 42 of the elongated shaft 28 of the outer ablation catheter 20, as shown in FIG. 1C. In a preferred embodiment, the distal section 52 of the elongated member 46 is pre-shaped to be placed in the expanded loop geometry, such that distal section 52 of the elongated member 46 automatically assumes the expanded loop geometry in response to the removal of a constraining force, such as that applied by the inner lumen 32 of the outer ablation catheter 20. The diameter of the expanded loop geometry of the distal section 52 of the elongated member 46 is slightly larger than the ostium of a typical pulmonary vein, e.g., in the range of 10-20 millimeters. Preferably, the distal section 52 of the elongated member 46 has a lateral stiffness that is less than the lateral stiffness of the stiffening plate 30 in the deflection direction of the distal section 40 of the elongated shaft 28. In this manner, the distal section 52 of the elongated member 46, when housed within the inner lumen 32 of the outer ablation catheter 20, does not excessively hinder the steerability of the distal section 52 of the elongated member 46.

In an optional embodiment, the distal section 52 of the elongated member 46 is radiopaque to enable visualization of the distal section 52 when deployed from the distal tip port 34 of the outer ablation catheter 20. For example, the distal section 52 of the elongated member 46 may be loaded within radiopaque particles, such as tungsten or bismuth.

In the illustrated embodiment, the ablative element(s) 48 are disposed along the distal section 52 of the elongated member 46. As a result, an ablative loop structure is formed at the distal end of the inner ablation catheter 22 when the distal section 52 is in the expanded loop geometry. In the illustrated embodiment, the ablative elements 48 take the form of ring electrodes, although in alternative embodiments, the ablative elements 46 can take other forms, e.g., chemical ablation lumens, ultrasonic transducers, microwave electrodes, ohmically heated hot wires, optical emitters, etc. The electrodes 48 may have any suitable length, e.g., in the range between 4 mm and 10 mm. The electrodes 48 may be composed of any suitable biocompatible, electrically conductive, material, e.g., platinum, gold, or stainless steel. In the illustrated embodiment, the electrodes 48 numbers eight, although in other embodiments, any plural number of ablative elements 48 can be provided.

In the illustrated embodiment, the electrodes 48 are solid discrete elements, although in alternative embodiments, the electrodes 48 may be formed by coating the exterior surface of the distal section 52 of the elongated member 46 with an electrically conducting material, like platinum or gold. The coating can be applied using sputtering, ion beam deposition, or equivalent techniques. The electrodes 48 can also be formed with a conductive ink compound that is pad printed onto distal section 52 of the elongated member 46. A preferred conductive ink compound is a silver-based flexible adhesive conductive ink (polyurethane binder), however other metal-based adhesive conductive inks such as platinum-based, gold-based, copper-based, etc., may also be used to form electrodes 48. Such inks are more flexible than epoxy-based inks. In another alternative embodiment, the electrodes 48 may take the form of wound, spiral coils. The coils can be made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility.

The electrodes 48 are electrically coupled to the mapping processor 12 (shown in FIG. 1), so that electrical events in myocardial tissue can be sensed for the creation of electrograms or monophasic action potentials (MAPs), or alternatively, isochronal electrical activity maps. To this end, signal wires (not shown) are respectively connected to the electrodes 48 using suitable means, such as soldering or welding. The signal wires are passed in a conventional fashion through a lumen (not shown) extending through the elongated member 46, where they are electrically coupled to the mapping processor 12 via the handle assembly 26, as will be described in further detail below. The electrodes 48 are also electrically coupled to the RF generator 14, so that the RF generator 14 may conduct coagulating energy to the electrodes 48. To this end, ablation wires (not shown) are respectively connected to the electrodes 48 using suitable means, such as soldering or welding. The ablation wires are passed in a conventional fashion through a lumen (not shown) extending through the elongated member 46, where they are electrically coupled to the RF generator 14 via the handle assembly 26, as will be described in further detail below.

In the illustrated embodiment, the steering element 24 takes the form of a steering wire, the distal end of which is affixed (e.g., soldered, spot welded, etc.) to the steering plate 30 in the distal section 52 of the elongated shaft 28 at an anchor point 25. The steering wire 24 is preferably composed of a soft and flexible material. In the illustrated embodiment, the steering wire 24 is external to the elongated shaft 28, although in alternative embodiments, the steering wire 24 may be disposed within the elongated shaft 28, e.g., in a steering lumen (not shown). As best shown in FIG. 3, in the illustrated embodiment, the steering wire 24 has a rectangular cross-section, thereby allowing the steering wire 24 to be more easily situation between the guide sheath 16 and the elongated shaft 28. In alternative embodiments, the steering wire 24 may have other cross-sections, e.g., circular. Tensioning of the steering wire 24 (i.e., pulling in the proximal direction) transforms the distal section 40 of the elongated shaft 28 from a straight configuration into a curved configuration. In the illustrated embodiment, the steering wire 24 not only has pull capability, but also has push capability, such that compression of the steering wire 24 (i.e., pushing in the distal direction) transforms the distal section 40 of the elongated shaft 26 back from the curved configuration into the straight configuration. To this end, the steering wire 24 may be composed of a polymer (e.g., poly-para-phenylene terephthalamide (commercially available under the trade name Kevlar®)) base 54 and metallic wires 56 longitudinally extending through the polymer base 54, as illustrated in FIG. 3. In an alternative embodiment, the steering wire 24 does not have push capability. Rather, relaxation of the steering wire 24 allows the resiliency of the distal section 40 of the elongated shaft 28 to transform it back from the curved configuration to the straight configuration.

The handle assembly 26 comprises a handle body 58 composed of a durable and rigid material, such as medical grade plastic, and ergonomically molded to allow a physician to more easily manipulate the EP catheter assembly 18. In the illustrated embodiment, the handle body 58 is hollow. The elongated shaft 28 of the outer ablation catheter 20 is affixed to the handle body 58, while the elongated member 46 and signal and ablation wires extend within the handle body 58.

The handle assembly 26 further comprises an ablation loop deployment/retraction actuator 60 (e.g., a piston) to which the elongated member 46 of the inner ablation catheter 22 is affixed, such that manipulation of the deployment/retraction actuator 60 in one direction 62a (e.g., in the proximal direction) retracts the distal section 52 of the elongated member 46 into the distal tip port 34, thereby placing it into its low-profile geometry (FIG. 1A), while manipulation of the deployment/retraction actuator 60 in the other direction 62b (e.g., in the distal direction) deploys the distal section 52 of the elongated member 46 from the distal tip port 34, thereby placing it into its expanded loop geometry (FIG. 1C).

The handle assembly 26 further comprises a steering actuator (e.g., a slider) 64 to which the steering wire 24 is affixed, such that manipulation of the steering actuator 64 deflects the distal section 40 of the elongated shaft 28 via the steering wire 24. That is, manipulation of the steering actuator 64 in one direction 66b tensions the steering wire 24, thereby transforming the distal section 40 of the elongated shaft 28 from its straight configuration to its curved configuration (FIG. 1B), while manipulation of the steering actuator 64 in the other direction 62a relaxes or pushes the steering wire 24, thereby transforming the distal section 40 of the elongated shaft 28 from its curved configuration to its straight configuration (FIG. 1A).

The handle assembly 26 further comprises an external connector 68, such as an external multiple pin connector, received in a port on the handle body 58. The signal and ablation wires from the electrodes 36 of the outer ablation catheter 20 and the electrodes 48 of inner ablation catheter 22 are coupled to the external connector 68, which in turn is coupled to the mapping processor 12 and RF generator 14 via a cable assembly 70, so that the mapping processor 12 and RF generator 14 can be functionally coupled to the EP catheter assembly 18. The handle assembly 26 may also include a printed circuit (PC) board (not shown) coupled to the external connector 60 and contained within the handle body 58.

Referring to FIGS. 5 and 6A-6K, one exemplary method 100 of using the tissue ablation system 10 to create lesions on endocardial tissue 206 of a patient to treat cardiac arrythmia suffered by the patient, and in particular, to create lesions on the endocardial surface 204 of the left atrium 202 of the heart 200 of the patient to treat AF (see FIG. 6A), will now be described. Advantageously, the distal section 52 of the inner ablation catheter 22 can be deployed from the distal tip port 34 of the outer ablation catheter 20, and deployed into its expanded loop geometry (i.e., an ablative loop structure) to create a circumferential lesion around the ostium 208 of at least one PV 206 (in the typical case at least one of four PVs) in the left atrium 202 of the heart 200, and then retracted within the distal tip port 34 of the outer ablation catheter 20, so that the distal section 40 of the outer ablation catheter 22 (i.e., the distal ablative structure), can be used without hindrance from the distal section 52 of the inner ablation catheter 22 to create linear and/or focal lesions along target lines 210 in the endocardial surface 204 of the heart 200 remote from the PVs 204. In this manner, multiple devices, and the associated introduction and removal of those devices, is not required to create the different lesions within the left atrium 202 of the heart 200.

Figure 6A:
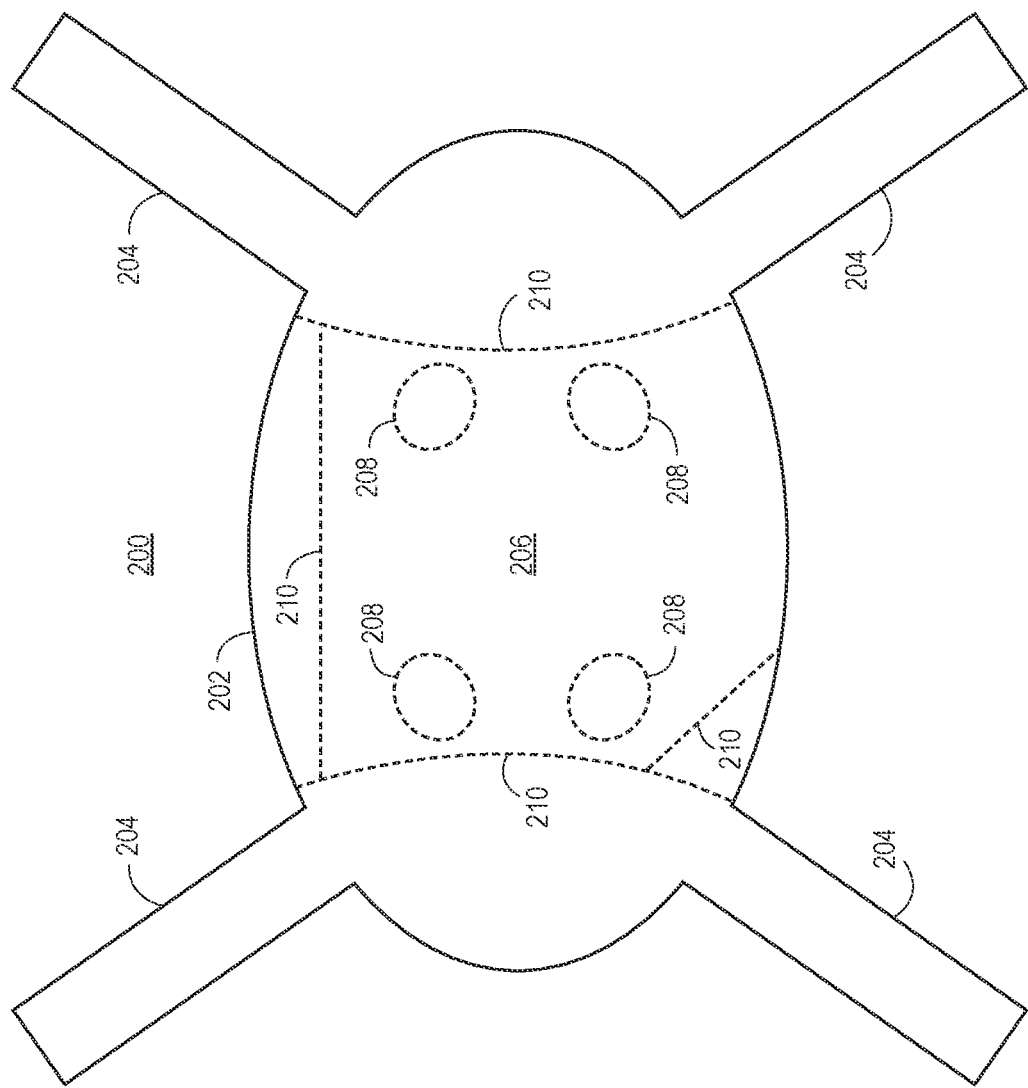
FIGS. 6A-6K are plan views illustrating the tissue ablation system of FIGS. 1A-1C in use to create lesions within the left atrium of the heart in accordance with the method of FIG. 5.
Figure 6B:
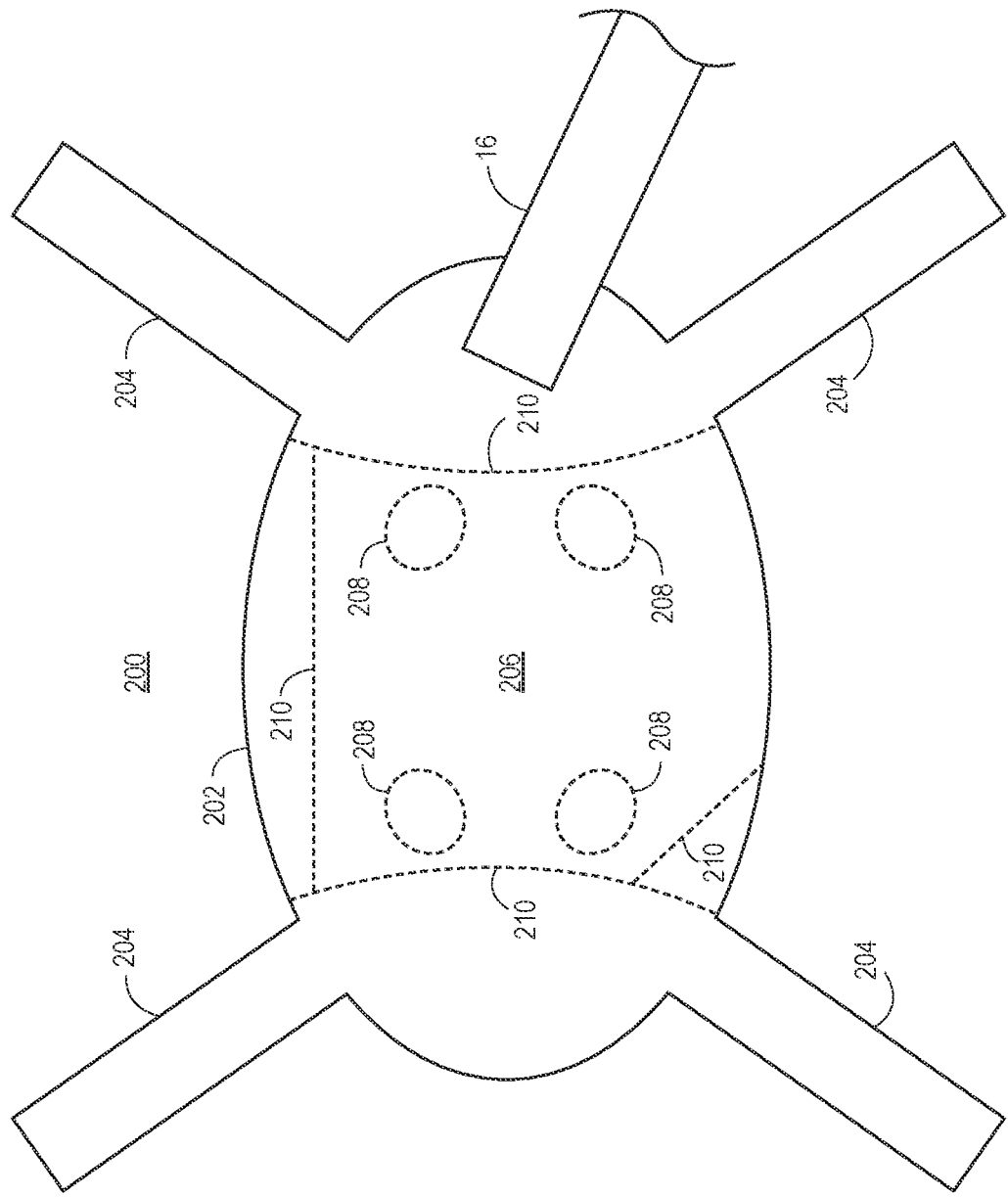

First, the guide sheath 16 is introduced into the left atrium 202 of the heart 200, so that the distal end of the guide sheath 16 (step 102) (see FIG. 6B). Introduction of the guide sheath 16 within the left atrium 202 can be accomplished using a conventional vascular introducer retrograde through the aortic and mitral valves, or can use a transeptal approach from the right atrium. A guide catheter or guide wire (not shown) may be used in association with the guide sheath 16 to aid in directing the guide sheath 16 through the appropriate artery toward the heart 200.

Figure 6C:
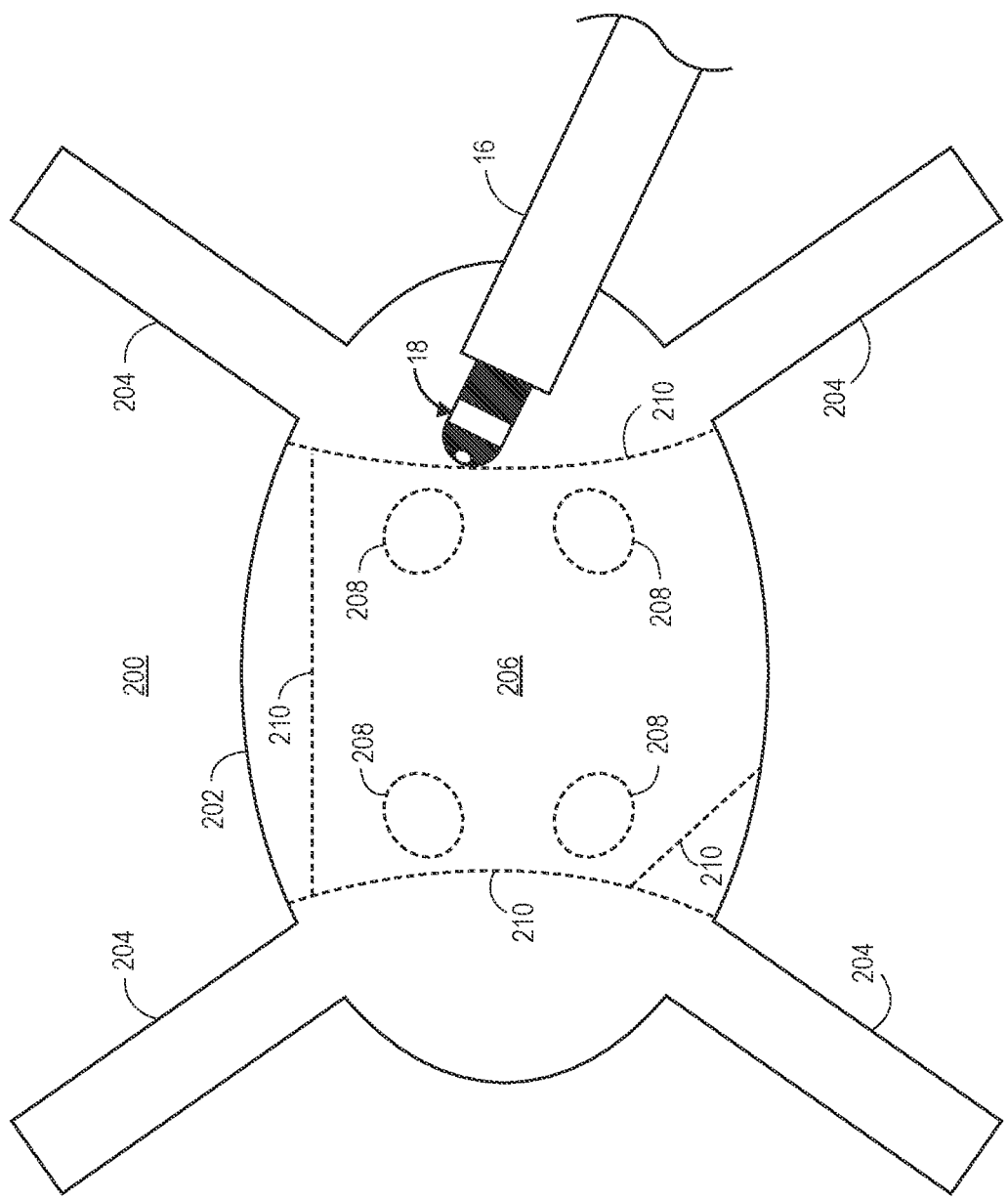
Figure 6D:
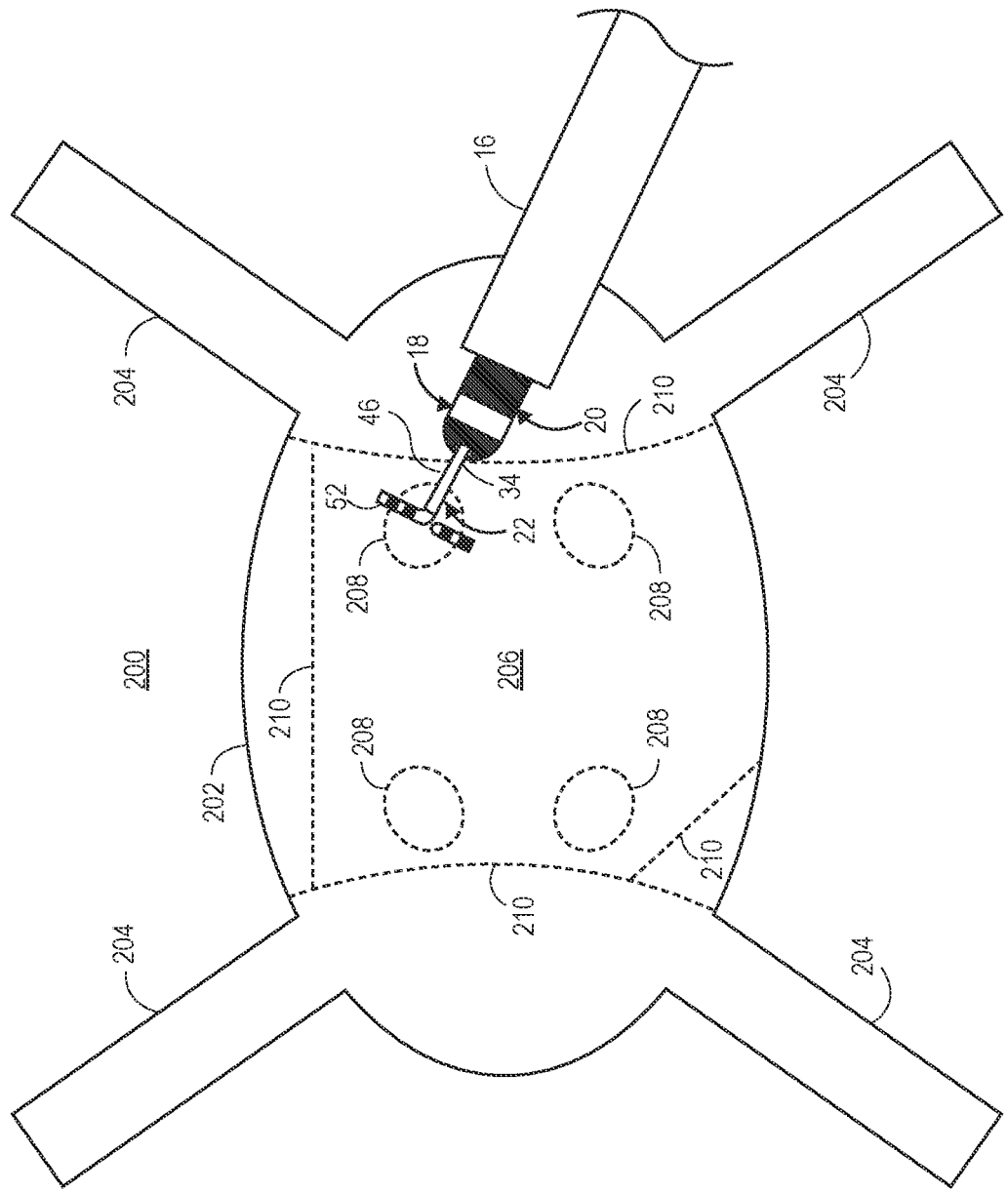

Once the distal end of the guide sheath 16 is properly placed, the EP catheter assembly 18, while the distal section 52 of the elongated member 46 of the inner ablation catheter 22 is in the low-profile geometry within the inner lumen 34 of the outer ablation catheter 20, is introduced through the guide sheath 16 until the distal end of the EP catheter assembly 18 is adjacent the ostium 208 of a selected PV 206 (step 104) (see FIG. 6C). The ablative loop structure of the inner ablation catheter 22 is then deployed from the outer ablation catheter 20. In particular, the elongated member 46 of the inner ablation catheter 22 is distally slid within the inner lumen 34 of the outer ablation catheter 20 (via manipulation of the ablation loop deployment/retraction actuator 60 of the handle assembly 26), thereby deploying the distal section 52 of the elongated member 46 of the inner ablation catheter 22 from the distal tip port 34 of the outer ablation catheter 20 (step 106) (see FIG. 6D).

Next, the ablative loop structure of the inner ablation catheter 22 is placed into an expanded loop geometry. In particular, the distal section 52 of the elongated member 46 of the inner ablation catheter 22 is placed into the expanded loop geometry (step 108) (see FIG. 6D). In the illustrated embodiment, the distal section 52 of the elongated member 46 of the inner ablation catheter 22 is automatically placed into the expanded loop geometry in response to releasing the constraining force of the inner lumen 34 of the outer ablation catheter 20 as the distal section 52 of the elongated member 46 of the inner ablation catheter 22 is deployed from the distal tip port 34 of the outer ablation catheter 20.

Figure 6E:
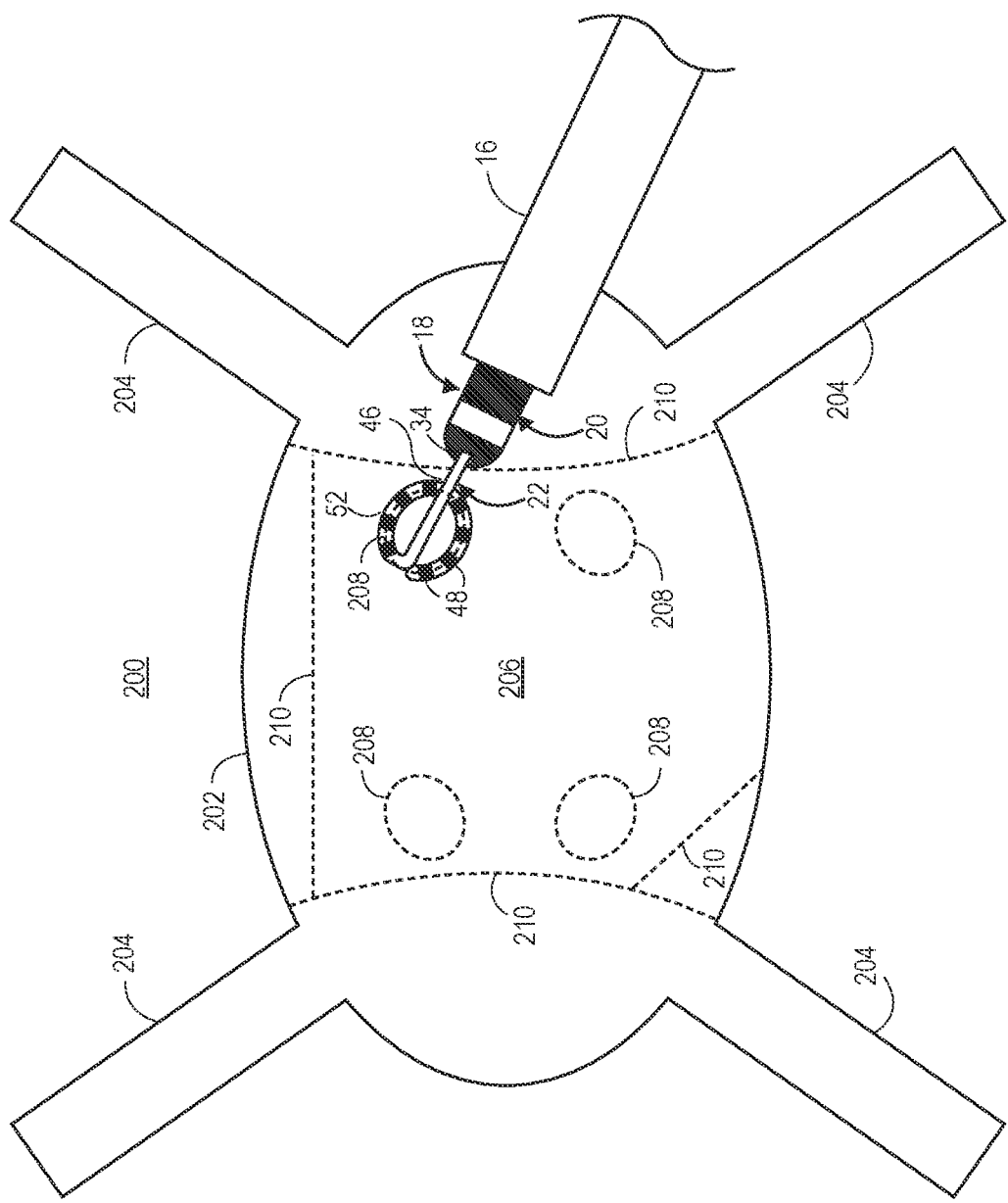
Figure 6F:
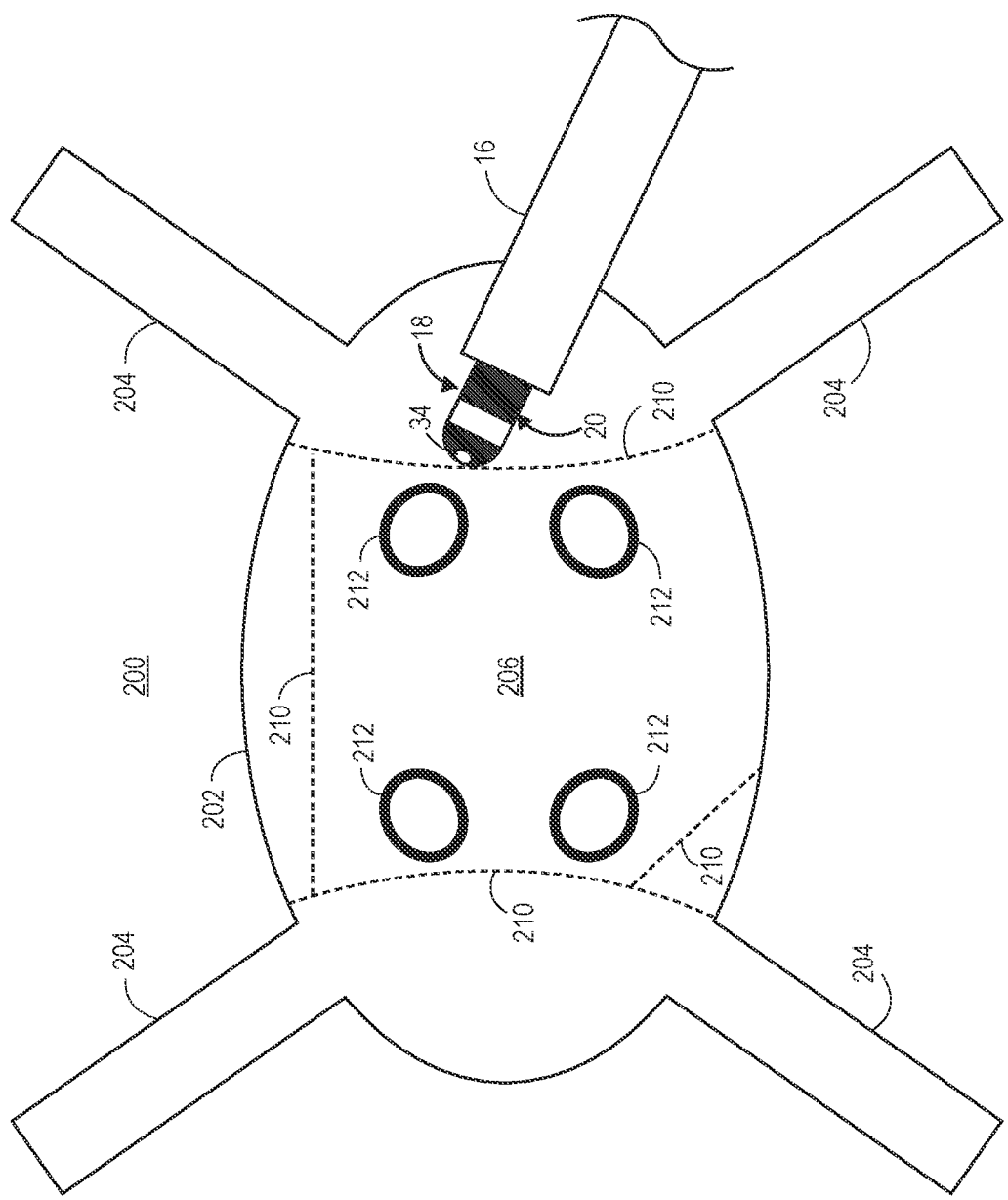
Figure 6G:
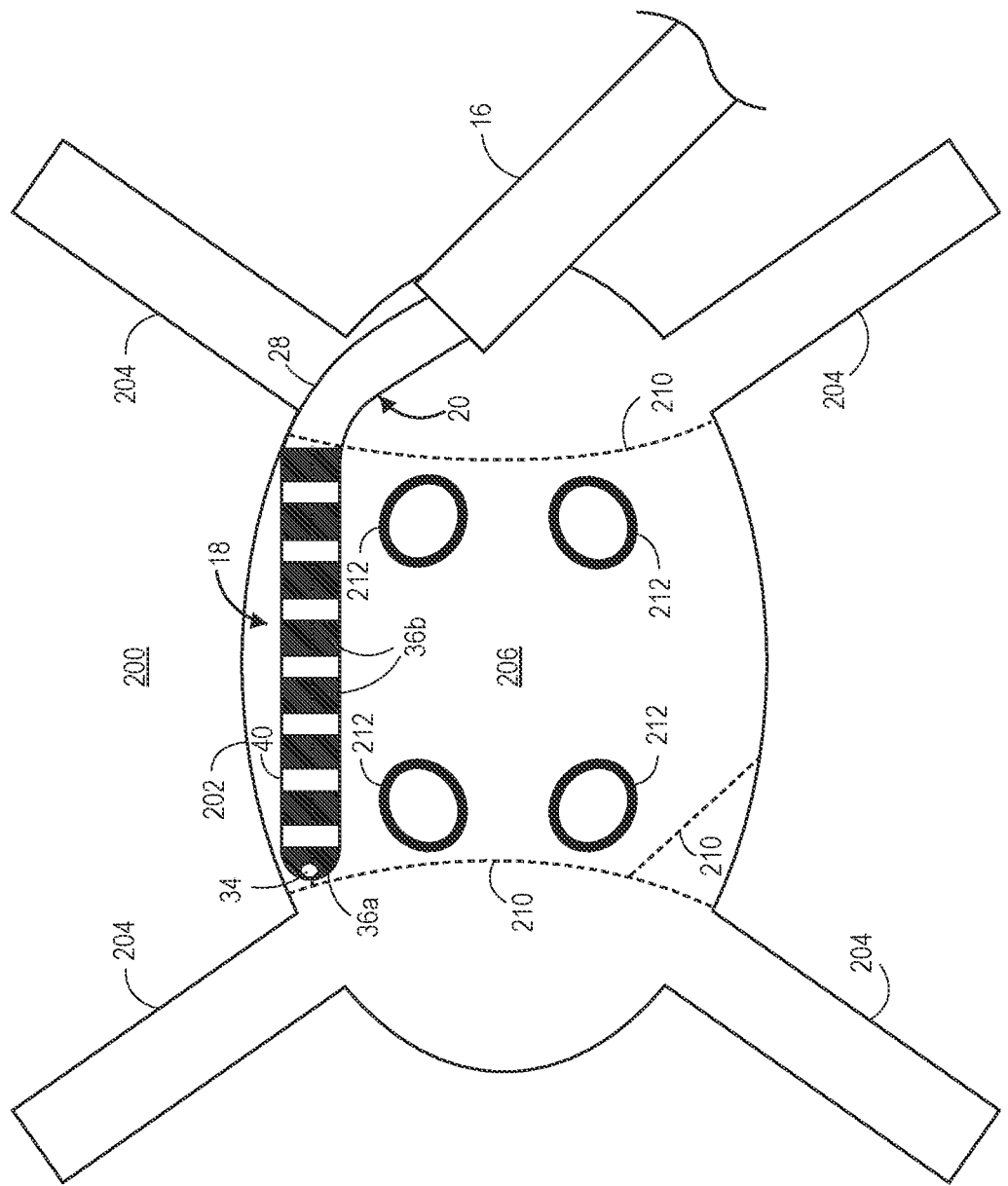

Next, the expanded ablative loop structure of the inner ablation catheter 22, and in particular, the distal section 52 of the elongated member 46 of the inner ablation catheter 22, when in the expanded loop geometry, is disposed on the endocardial tissue 206 around the ostium 208 of the PV 206 (step 110) (see FIG. 6E). The distal section 40 of the elongated shaft 28 of the outer ablation catheter 20 may be deflected (via manipulation of the steering actuator 62 of the handle assembly 26) in order to manipulate the distal section 52 into contact with the endocardial tissue 206 around the ostium 208 of the PV 206. The resiliency of the distal section 52 places the electrodes 48 in firm and stable contact with the endocardial tissue 206. Once electrode contact has been achieved, the mapping processor 12 is operated in order to obtain and record pre-ablation ECG signals from the distal section 40 of the elongated shaft 28 of the outer ablation catheter 20 at the endocardial tissue 206 around the ostium 208 of the PV 206 (step 112). As described below, these ECG signals will be compared with the ECG signals obtained subsequent to an ablation procedure in order to determine if the resultant lesion has successfully electrically isolated the PV 206 from the left atrium 202 of the heart 200.

Once the pre-ablation ECG signals have been obtained from the electrodes 48 and recorded, the ablative loop structure of the inner ablation catheter 22 is activated (by operating the RF generator 14 in order to convey RF energy to the electrodes 48), thereby creating a circumferential lesion 212 (see FIG. 6F) in the endocardial tissue 206 around the ostium 208 of the PV 206 (step 114). In one method, the RF energy is conveyed to the electrodes 48 one at a time. Thus, assuming that there are eight electrodes 48, eight ablation procedures are performed in order to create the circumferential lesion 212 in the endocardial tissue 206 around the ostium 208 of the PV 206. Alternatively, the RF energy is simultaneously conveyed to all eight electrodes 48. In this manner, a single ablation procedure ("single shot") is performed in order to create the circumferential lesion 212 in the endocardial tissue 206 around the ostium 208 of the PV 206. In either case, the electrodes 48 need not be moved during the ablation procedure(s).

After the circumferential lesion 212 has been created, the mapping processor 12 is again operated to obtain and record post-ablation ECG signals from the distal section 40 of the elongated shaft 28 of the outer ablation catheter 20 at the endocardial tissue 206 around the ostium 208 of the PV 206 (step 116). The post-ablation ECG signals are the compared to the pre-ablation ECG signals to confirm that the circumferential lesion has completely isolated the PV 206 from the left atrium 202 of the heart 200 (step 118). Additional circumferential lesions 212 can be created in the endocardial tissue 206 around the ostia 208 of other PVs 206 by repeating steps 110-118 (see FIG. 6F).

Next, the ablative loop structure of the inner ablation catheter is retracted within the outer ablation catheter 20. In particular, the elongated member 46 of the inner ablation catheter 22 is proximally slid within the inner lumen 34 of the outer ablation catheter 20 (via manipulation of the ablation loop deployment/retraction actuator 60 of the handle assembly 26), thereby retracting the distal section 52 of the elongated member 46 of the inner ablation catheter 22 into the distal tip port 34 of the outer ablation catheter 20 (step 120) (see FIG. 6F).

Next, the ablative distal end of the outer ablation catheter 20, when the ablative loop structure of the inner ablation catheter 22 is in the inner lumen 34 of the outer ablation catheter 20, is disposed at a target region of the endocardial tissue 206 remote from the ostium 208 of the PV 206. In particular, the distal section 40 of the elongated shaft 28 of the outer ablation catheter 20, while the distal section 52 of the elongated member 46 of the inner ablation catheter 22 is in the low-profile geometry within the inner lumen 34 of the outer ablation catheter 20, is disposed at a target line 210 along the endocardial tissue 206 remote from the ostium 208 of the PV 206 (step 122) (see FIG. 6G). The distal section 40 of the elongated shaft 28 of the outer ablation catheter 20 may be deflected (via manipulation of the steering actuator 62 of the handle assembly 26) in order to manipulate the distal section 40 into contact with the target line. The resiliency of the distal section 40 places the electrodes 36 in firm and stable contact with the endocardial tissue 206.

Once electrode contact has been achieved, the mapping processor 12 is operated in order to obtain and record pre-ablation ECG signals from the distal section 40 of the elongated shaft 28 of the outer ablation catheter 20 at the endocardial tissue 206 along the target line 210 (step 124). In one method, the ablative distal tip of the outer ablation catheter 20, and in particular, the cap electrode 36a, is iteratively disposed at different points along the target line 210 of the endocardial tissue 206 and the mapping processor 12 operated, thereby iteratively obtaining and recording the pre-ablation ECG signals from the target line 210 along the endocardial tissue 206. In another method, the ablative distal section of the outer ablation catheter 20, and in particular, the cap electrode 36a and ring electrodes 36b, are disposed along the target line 210 of the endocardial tissue 206 and the mapping processor 12 operated, thereby obtaining and recording the pre-ablation ECG signals from the target line 210 along the endocardial tissue 206 without requiring the ablative distal section of the outer ablation catheter 20 to be moved multiple times.

Figure 6H:
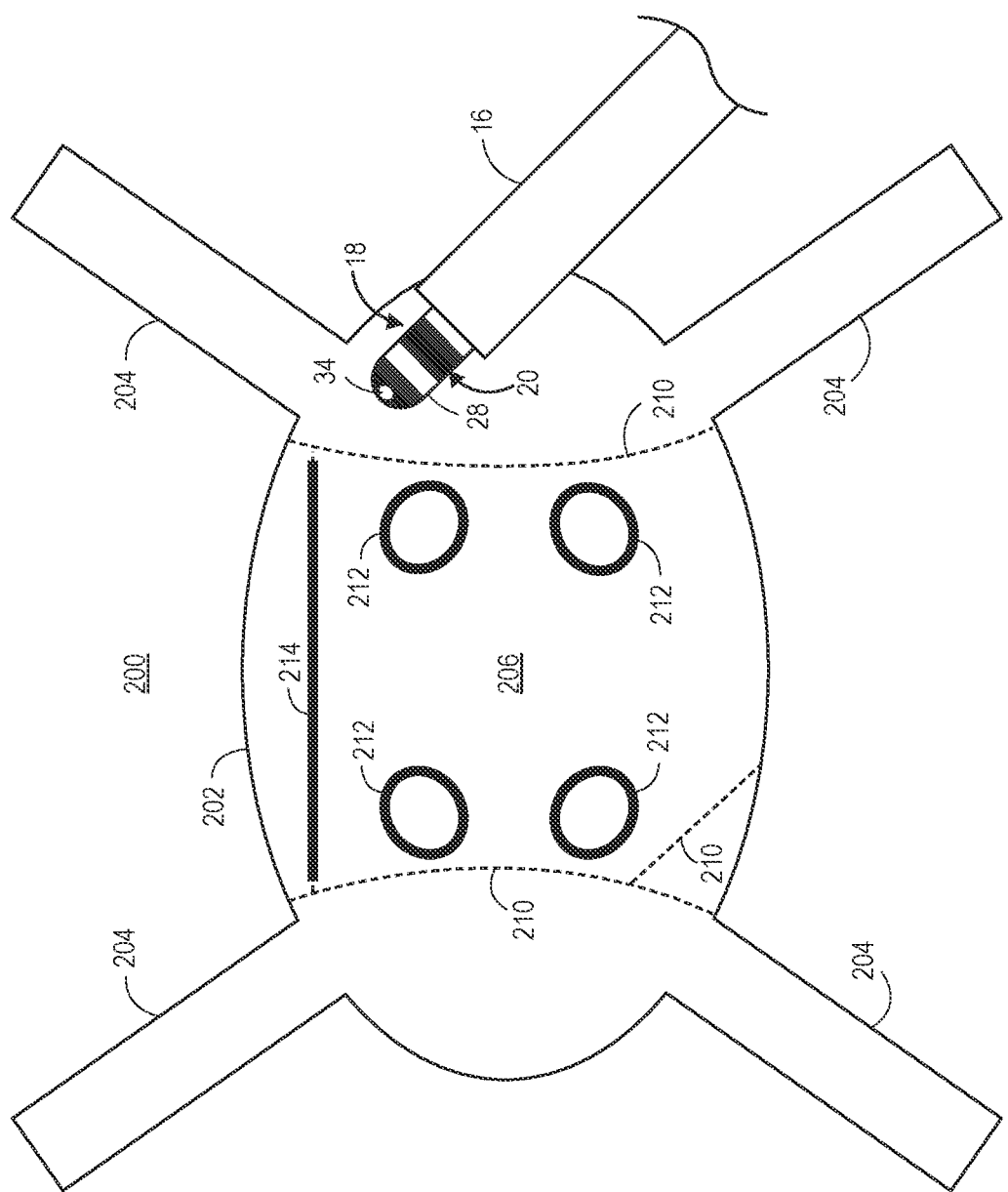
Figure 6I:
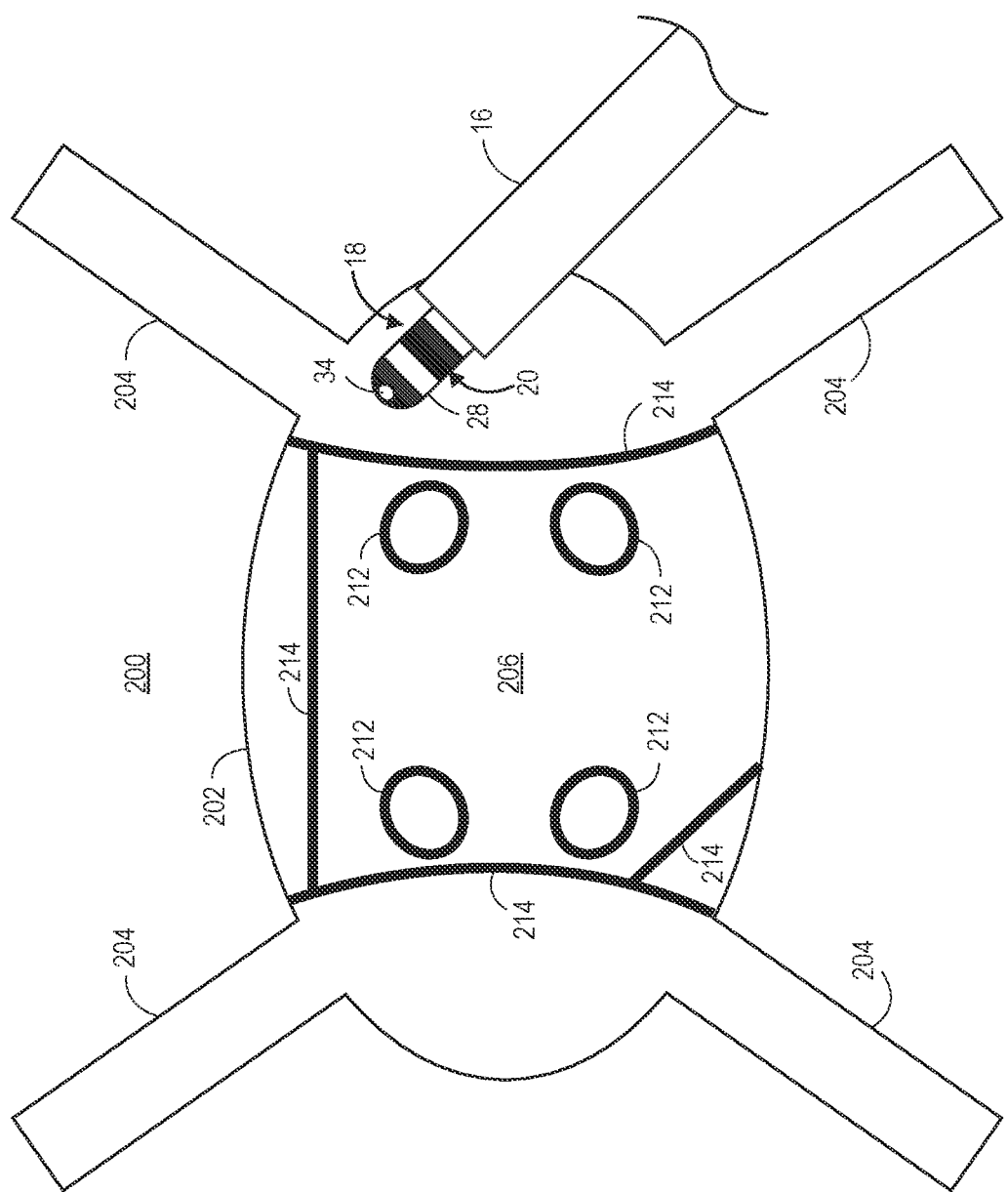
Figure 6J:
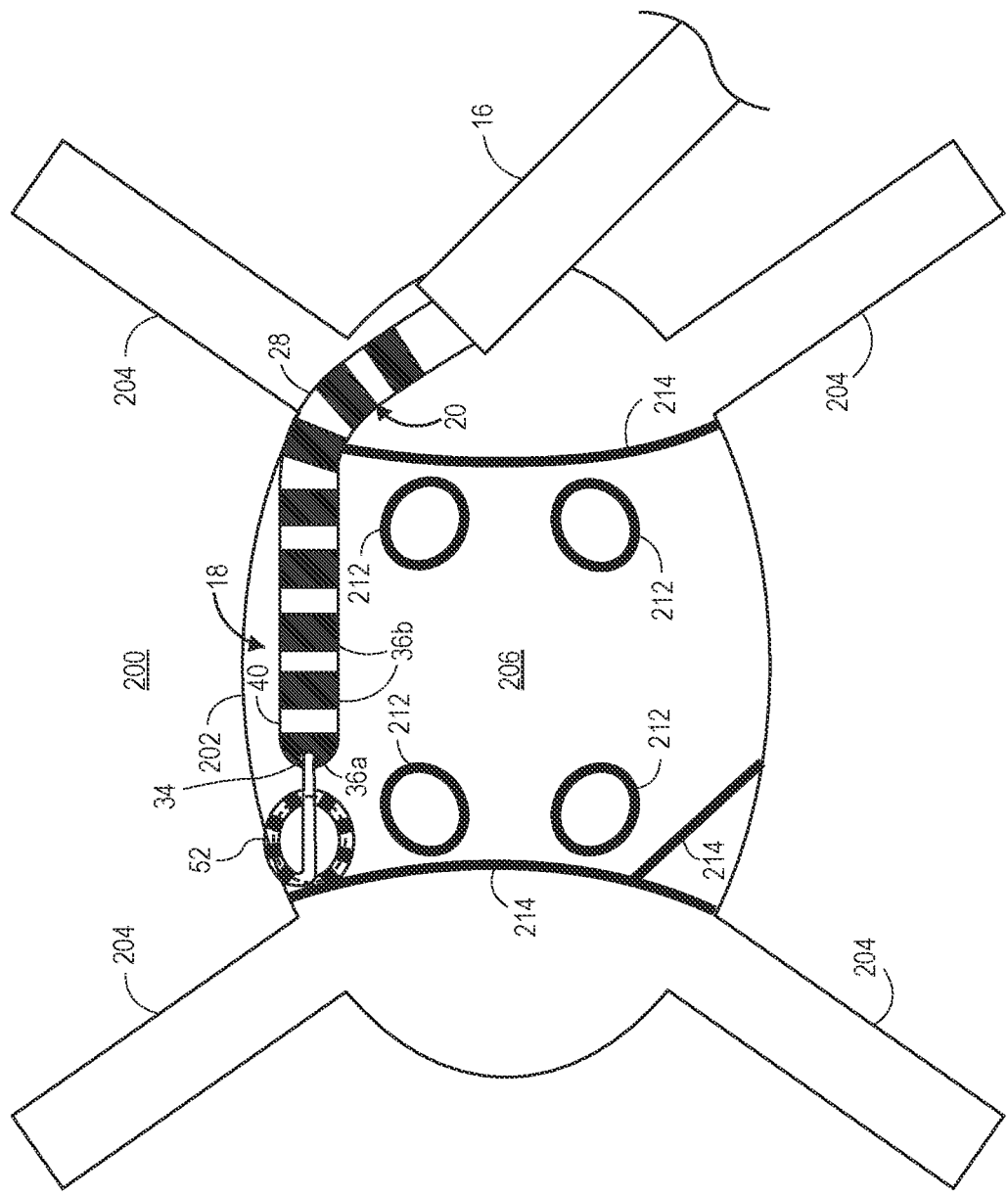

Once the pre-ablation ECG signals have been obtained from the electrodes 36 and recorded, the ablative distal end of the outer ablation catheter 20 is activated (by operating the RF generator 14 in order to convey RF energy to the electrodes 36), thereby creating a linear lesion in the endocardial tissue 206 along the target line 210 (step 126) (see FIG. 6H). In one method, the ablative distal tip of the outer ablation catheter 20, and in particular, the cap electrode 36*a*, is iteratively disposed at different points along the target line 210 of the endocardial tissue 206 and the ablative distal tip activated (by operating the RF generator 14 in order to convey RF energy to the electrodes 36), thereby iteratively creating a linear lesion in the endocardial tissue 206 along the target line 210. In another method, the ablative distal end of the outer ablation catheter 20, and in particular, the cap electrode 36*a* and ring electrodes 36*b*, are disposed along the target line 210 of the endocardial tissue 206 and the ablative distal end activated (by operating the RF generator 14 in order to convey RF energy to the electrodes 36), thereby iteratively creating the linear lesion in the endocardial tissue 206 along the target line 210. In this case, the RF energy may be conveyed to the electrodes 36 one at a time. Thus, assuming that there are six electrodes 36, six ablation procedures are performed in order to create the linear lesion in the endocardial tissue 206 along the target line 210. Alternatively, the RF energy is simultaneously conveyed to all six electrodes 36. In this manner, a single ablation procedure ("single shot") is performed in order to create the linear lesion in the endocardial tissue 206 along the target line 210. In either case, the electrodes 36 need not be moved during the ablation procedure(s).

After the linear lesion has been created, the mapping processor 12 is again operated to obtain and record post-ablation ECG signals from the electrodes 36 at the endocardial tissue 206 along the target line 210 (step 128). The post-ablation ECG signals are then compared to the pre-ablation ECG signals to confirm that the region on one side of the target line 210 is completely isolated from the region on the other side of the target line 210 (step 130). Additional linear lesions 214 can be created in the endocardial tissue 206 by repeating steps 122-130 (see FIG. 6I).

Although the method 100 has been described as creating the circumferential lesions 212 prior to creating the linear lesions 214, it should be appreciated that alternative methods may create linear lesions prior to circumferential lesions. In this case, linear lesions 214 are created in the endocardial tissue 206 along the target lines 210 prior to initially deploying the ablative loop structure of the inner ablation catheter 22 from the outer ablation catheter 20, the ablative loop structure of the inner ablation catheter 22 is then deployed from the outer ablation catheter 20 to create the circumferential lesions 212 in the endocardial tissue 206, and then the ablative loop structure of the inner ablation catheter 22 is retracted within the outer ablation catheter 20 after the creation of the circumferential lesions 212 in the endocardial tissue 206.

Figure 6K:
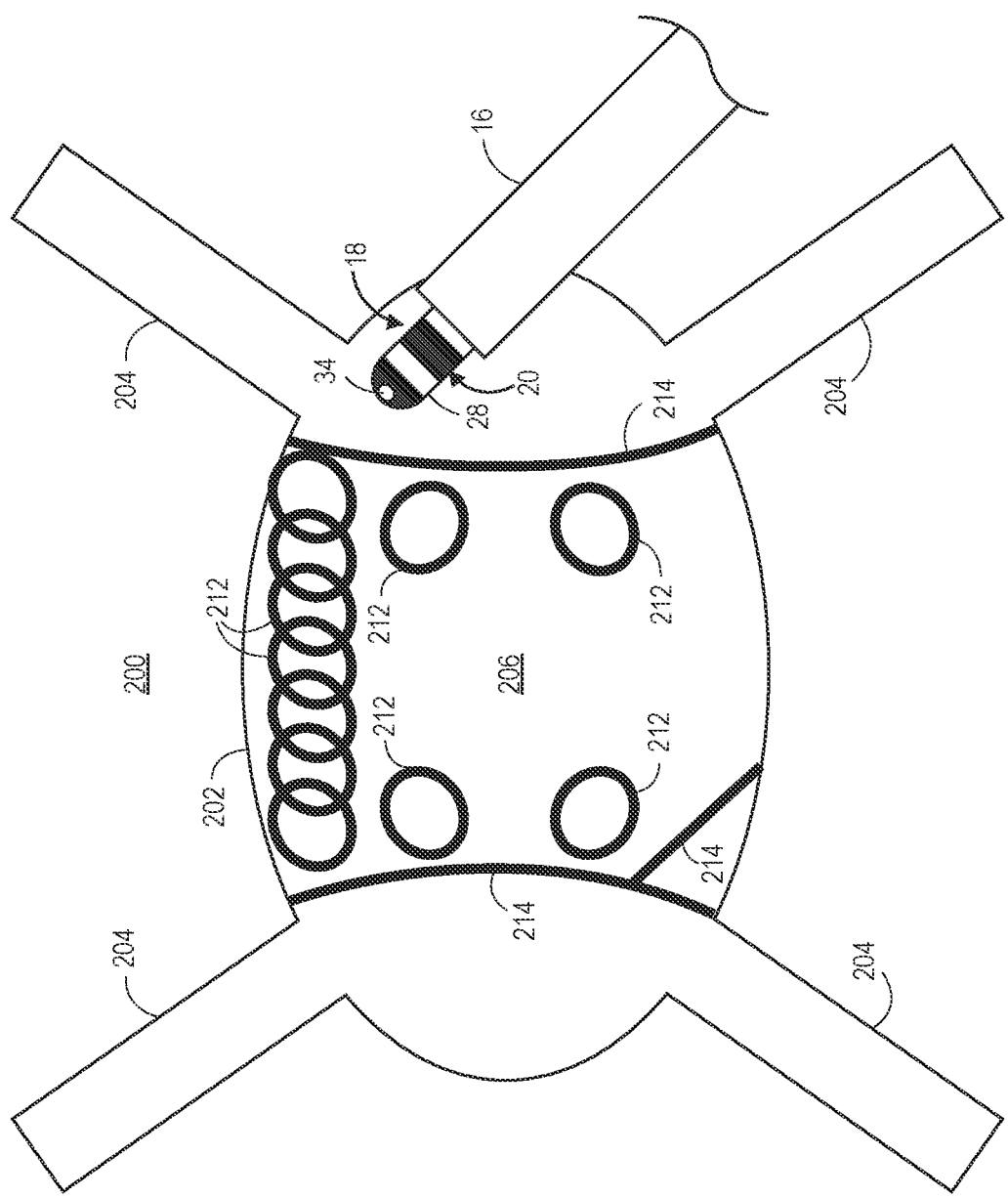

In an alternative method, the expanded ablative loop structure of the inner ablation catheter 22, and in particular, the distal section 52 of the elongated member 46 of the inner ablation catheter 22, when in the expanded loop geometry, is iteratively disposed on the endocardial tissue 206 on different points along the target line 210 (see FIG. 6J), and the ablative loop structure of the inner ablation catheter 22 is iteratively activated (by operating the RF generator 14 in order to convey RF energy to the electrodes 48), thereby creating a series of circumferential lesions 212 in the endocardial tissue 206 along the target line 210 (see FIG. 6K).

After, the circumferential lesions 212 and linear lesions 214 are created in the endocardial tissue 206, the guide catheter 16 and EP catheter assembly 18 are removed from the left atrium 202 of the heart 200 (step 132).

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A method of ablating endocardial tissue of a patient using an ablation catheter assembly having an elongated shaft having an ablative shaft distal end comprising at least one ablative element and a distal tip port distal to the at least one ablative element, and an ablative loop structure housed within the elongated shaft, the method comprising:
   introducing the ablation catheter assembly into a heart chamber of the patient while the ablative loop structure is housed within the elongated shaft;
   deploying the ablative loop structure from the elongated shaft via the distal tip port;
   placing the ablative loop structure in an expanded geometry;
   disposing the expanded ablative loop structure on the endocardial tissue around an ostium of a blood vessel extending from the heart chamber;
   activating the ablative loop structure, thereby creating a circumferential lesion around the ostium of the blood vessel;
   disposing the at least one ablative element, when the ablative loop structure is housed within the elongated shaft, at a target region of the endocardial tissue remote from the ostium of the blood vessel; and
   activating the at least one ablative element, thereby creating another lesion at the target region.

2. The method of claim 1, wherein the ablative loop structure assumes the expanded geometry in response to deploying the ablative loop structure from the elongated shaft.

3. The method of claim 1, wherein the heart chamber is a left atrium, and the blood vessel is a pulmonary vein.

4. The method of claim 1, further comprising retracting the ablative loop structure within the elongated shaft via the distal tip port after creating the circumferential lesion around the ostium of the blood vessel, but prior to disposing the at least one ablative element at the target site of the endocardial tissue.

5. The method of claim 1, wherein the target region is a target line.

6. The method of claim 5, wherein disposing the at least one ablative element at the target region of the endocardial tissue and activating the at least one ablative element comprises iteratively disposing a single one of the at least one ablative element at different points along the target line of the endocardial tissue and activating the single one of the at least one ablative element, thereby iteratively creating the other lesion along the target line.

7. The method of claim 5, wherein the ablative shaft distal end comprises a linear array of ablative elements, and wherein disposing the at least one ablative element at the target region of the endocardial tissue and activating the at least one ablative element comprises disposing the linear array of ablative elements along the target line of the endocardial tissue and activating the the linear array ablative elements, thereby creating the other lesion along the target line.

8. The method of claim 1, wherein the patient has a cardiac arrhythmia, and the circumferential lesion and other lesion treats the cardiac arrhythmia.

9. The method of claim 1, wherein the ablation catheter assembly is introduced into the heart chamber of the patient via a vasculature of the patient.

* * * * *